(12) United States Patent
Pickering et al.

(10) Patent No.: US 8,623,820 B2
(45) Date of Patent: Jan. 7, 2014

(54) FGF-9 AND ITS USE RELATING TO BLOOD VESSELS

(75) Inventors: J. Geoffrey Pickering, London (CA); Zengxuan Nong, London (CA); Matthew Frontini, London (CA)

(73) Assignee: University of Western Ontario, London, Ontario ( * ) Notice: Subject to any disclaimer, the term of this patent is extended or adjusted under 35 U.S.C. 154(b) by 13 days.

(21) Appl. No.: 12/990,745

(22) PCT Filed: May 1, 2009

(86) PCT No.: PCT/CA2009/000586
§ 371 (c)(1),
(2), (4) Date: Jan. 6, 2011

(87) PCT Pub. No.: WO2009/132457
PCT Pub. Date: Nov. 5, 2009

(65) Prior Publication Data
US 2011/0104132 A1    May 5, 2011

Related U.S. Application Data

(60) Provisional application No. 61/050,143, filed on May 2, 2008.

(51) Int. Cl.
*A61K 38/18* (2006.01)
*C07K 14/50* (2006.01)

(52) U.S. Cl.
USPC .......................................... 514/9.1; 514/13.3

(58) Field of Classification Search
None
See application file for complete search history.

(56) References Cited

U.S. PATENT DOCUMENTS

| | | | |
|---|---|---|---|
| 4,956,455 | A | 9/1990 | Baird |
| 5,155,214 | A | 10/1992 | Baird |
| 5,302,702 | A | 4/1994 | Seddon |
| 5,314,872 | A | 5/1994 | Kato |
| 5,352,589 | A | 10/1994 | Bergonzoni |
| 5,371,206 | A | 12/1994 | Seddon |
| 5,387,673 | A | 2/1995 | Seddon |
| 5,439,818 | A | 8/1995 | Fiddes |
| 5,491,220 | A | 2/1996 | Seddon |
| 5,514,566 | A | 5/1996 | Fiddes |
| 5,604,293 | A | 2/1997 | Fiddes |

FOREIGN PATENT DOCUMENTS

| | | |
|---|---|---|
| CA | 2590338 | 8/2000 |
| CA | 2483602 | 11/2003 |
| WO | WO00/21548 | 4/2000 |
| WO | WO98/50079 | 12/2004 |

OTHER PUBLICATIONS

Santo-Ocampo, Expression and Biological Activity of Mouse Fibroblast Growth Factor-9, JBC, vol. 271 (3), pp. 1726-1731.*
Torchilin et al, Peptide and protein drug delivery to and into tumors: challenges and solutions, DDT, 2003, vol. 8(6), pp. 259-266.*
Guo et al, Protein tolerance to random amino acid change, PNAS, 2004, vol. 101 (25), pp. 9205-9210.*
Lesk et al, Prediction of Protein Function from Protein Sequence and Structure, p. 27 and 28, downloaded Sep. 16, 2007.*
White et al, FGF9 and SHH regulate mesenchymal Vegfa expression and development of the pulmonary capillary network, Development and Disease, 2007, pp. 3743-3752.*
Frontini et al, Abstract 3602—Fibroblast Growth Factor-9 Stabilizes Angiogenesis and Generates Vasoresponsive Microvessels, Circulation, 2008, 2 pages.*
Santo-Ocampo, Expression and Biological Activity of Mouse Fibroblast Growth Factor-9, JBC, Jan. 19, 1996, vol. 271 (3), pp. 1726-1731.*
Nagatoro T et al; Angiogenesis and Fibroblast Growth Factors (FGFs) in a Three-Dimensional Collagen Gel Culture; Okajimas Folia Anat. Jpn., May 2003, vol. 80(1): p. 7-14, ISSN: 0030-154X.
White AC et al; FGF9 and SHH Regulate Mesenchymal Vegfa Expression and Development of the Pulmonary Capillary Network Development, Oct. 2007, vol. 134(20): p. 3743-3752, ISSN: 0950-1991.
Duplan SM et al.; Antitumor Activity of Fibroblast Growth Factors (FGFs) for Medulloblastoma May Correlate with FGF Receptor Expression and Tumor Variant; Clin. Cancer Res., Jan. 2002, vol. 8(1): p. 246-257, ISSN: 1078-0432.
Matsumoto-Yoshitomi S; Autocrine Transformation by Fibroblast Growth Factor 9 (FGF-9) and its Possible Participation in Human Oncogenesis; Int. J. Cancer, May 2, 1997 (Feb. 5, 1997), vol. 71(3): p. 442-450, ISSN: 0020-7136.
Todo T et al.; Expression and Growth Stimulatory Effect of Fibroblast Growth Factor 9 in Human Brain Tumors; Neurosurgery, Aug. 1998, vol. 43(2): p. 337-346, ISSN: 0148-396X.
Fakhry et al.; Effects of FGF-2/-9 in Calvarial Bone Cell Cultures: Differentiation Stage-Dependent Mitogenic Effect, Inverse Regulation of BMP-2 and Noggin, and Enhancement of Osteogenic Potential Bone, Feb. 2005, vol. 36(2): p. 254-266, ISSN: 8756-3282.

* cited by examiner

*Primary Examiner* — David Romeo
(74) *Attorney, Agent, or Firm* — Sim & McBurney

(57) ABSTRACT

There is provided a composition for controlling formation and/or stabilization of a blood vessel comprising a first isolated nucleic acid molecule that encodes a FGF-9 polypeptide and optionally one or more isolated nucleic acid molecule that encodes another angiogenic polypeptide. There is provided a composition for controlling formation and/or stabilization of a blood vessel comprising administering an effective amount of a composition comprising an isolated FGF-9 polypeptide and one or more other angiogenic polypeptides. The compositions provided herein may be useful for controlling angiogenesis and/or vasculogenesis.

5 Claims, 20 Drawing Sheets mRNA coding region sequence and corresponding amino acid sequnce for mammalian FGF-9. A) Homo sapiens (NCBI gi:391718), B) Mus musculus (NCBI gi:1161346) C) Rattus norvegicus (NCBI gi:391852)

FIGURE 1

FGF-9 Amino Acid Alignment

```
FGF-9_Human/1-208    1  MAPLG VGN FGV  AVPFG VPVLPV SPVLLS   LG S AGGLP 46
FGF-9_Mouse/1-208    1  MAPLG VGS FGV  AVPFG VPVLPV SPVLLN   LG    AGGLP 46
FGF-9_Rat/1-208      1  MAPLG VGS FGV  AVPFG VPVLPV SPVLLS   LG    AGGLP 46
FGF-9_Pig/1-208      1  MAPLG VGN FGV  AVPFG VPVLPV SPVLL    LS    AGGLP 46

FGF-9_Human/1-208   47  GPAV   L  L GI L    QL    GF L  I FPNG   QG       F 92
FGF-9_Mouse/1-208   47  GPAV   L  L GI L    QL    GF L  I FPNG   QG       F 92
FGF-9_Rat/1-208     47  GPAV   L  L GI L    QL    GF L  I FPNG   QG       F 92
FGF-9_Pig/1-208     47  GPAV   L  L GI L    QL    GF L  I FPNG   QG       F 92

FGF-9_Human/1-208   93  G L   F S AVGLVS   GV SGL LGMN    L GS   L    GVF  138
FGF-9_Mouse/1-208   93  G L   F S AVGLVS   GV SGL LGMN    L GS   L    GVF  138
FGF-9_Rat/1-208     93  G L   F S AVGLVS   GV SGL LGMN    L GS   L    GVF  138
FGF-9_Pig/1-208     93  G L   F S AVGLVS   GV SGL LGMN    L GS   L    GVF  138

FGF-9_Human/1-208  139  QF   NW NT SSNL   V TG    VALN  GTP  G      Q  F 184
FGF-9_Mouse/1-208  139  QF   NW NT SSNL   V TG    VALN  GTP  G      Q  F 184
FGF-9_Rat/1-208    139  QF   NW NT SSNL   V TG    VALN  GTP  G      Q  F 184
FGF-9_Pig/1-208    139  QF   NW N  SSNL   V TG  F VALN  G P  G      Q  F 184

FGF-9_Human/1-208  185   FLP PV P  VP L    LS S   (SEQ ID NO:1)   208
FGF-9_Mouse/1-208  185   FLP PV P  VP L    LS S   (SEQ ID NO:2)   208
FGF-9_Rat/1-208    185   FLP PV P  VP L    LS S   (SEQ ID NO:3)   208
FGF-9_Pig/1-208    185   FLP PV P  VP L    LS S   (SEQ ID NO:4)   208
```

FIGURE 2

Secreted Factors Upregulated During SMC Maturation
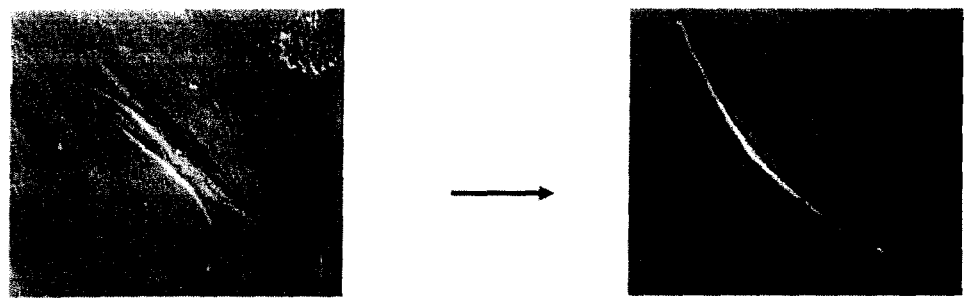
2023 Secreted Factors Screened (Affymetric U133)
↓
1087 Secreted Factors Potentially Expressed by SMCs
↓
488 Potentially Secreted Factors Upregulated
↓
27 Secreted Factors Statistically Upregulated
↓
Fibroblast Growth Factor-9
immature  mature
 FGF-9
FIGURE 3

FGF-9 is Uniquely Upregulated in Contractile SMCs

|  | Undetected | Unchanged | Downregulated $(p<0.05)$ | Upregulated $(p<0.05)$ |
|---|---|---|---|---|
| FGF | FGF-3  FGF-17<br>FGF-6  FGF-19<br>FGF-8  FGF-20<br>FGF-10 FGF-22<br>FGF-13 FGF-23 | FGF-7<br>FGF-11<br>FGF-12<br>FGF-14<br>FGF-18 | FGF-1<br>FGF-2<br>FGF-5 | FGF-9 |
| FGF Receptor | FGFR-4 | FGFR-1<br>FGFR-2<br>FGFR-3 | | |

FIGURE 4

*In vitro* Vasculogenesis

A
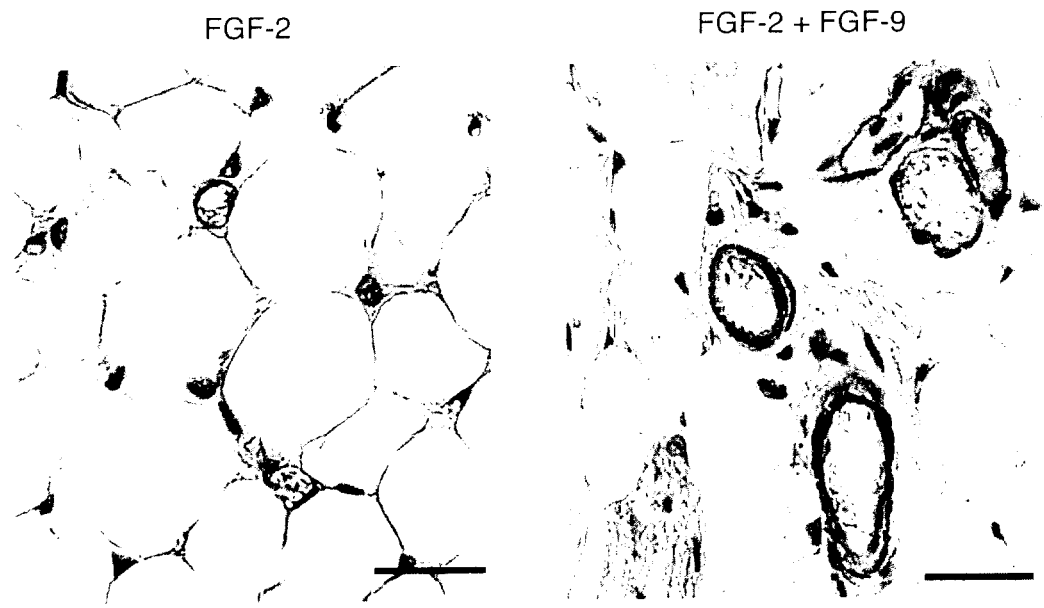
B
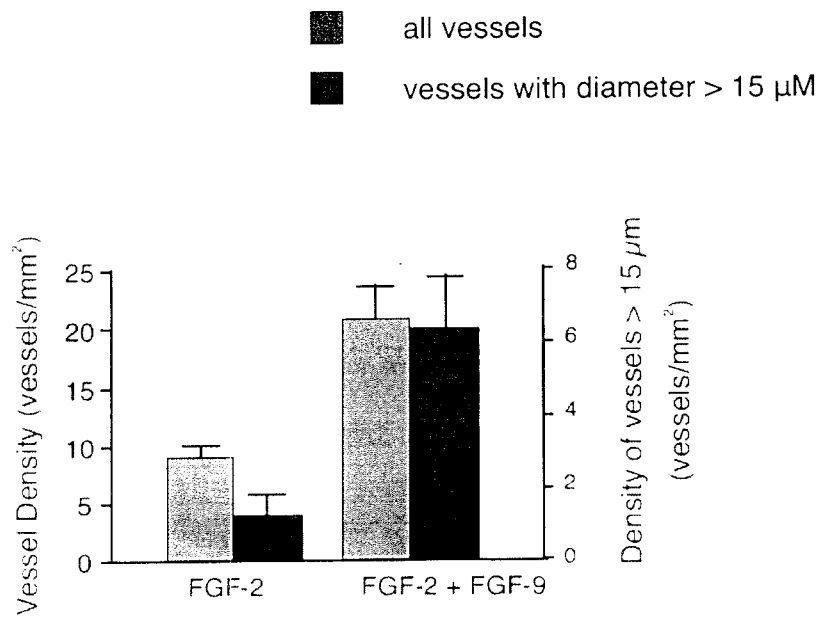
FIGURE 12

SEQUENCE LISTING

<160> NUMBER OF SEQ ID NOS: 4

<210> SEQ ID NO 1
<211> LENGTH: 208

<212> TYPE: PRT
<213> ORGANISM: Homo sapiens

<400> SEQUENCE: 1

```
Met Ala Pro Leu Gly Glu Val Gly Asn Tyr Phe Gly Val Gln Asp Ala
1               5                   10                  15

Val Pro Phe Gly Asn Val Pro Val Leu Pro Val Asp Ser Pro Val Leu
            20                  25                  30

Leu Ser Asp His Leu Gly Gln Ser Glu Ala Gly Gly Leu Pro Arg Gly
        35                  40                  45

Pro Ala Val Thr Asp Leu Asp His Leu Lys Gly Ile Leu Arg Arg Arg
    50                  55                  60

Gln Leu Tyr Cys Arg Thr Gly Phe His Leu Glu Ile Phe Pro Asn Gly
65                  70                  75                  80

Thr Ile Gln Gly Thr Arg Lys Asp His Ser Arg Phe Gly Ile Leu Glu
                85                  90                  95

Phe Ile Ser Ile Ala Val Gly Leu Val Ser Ile Arg Gly Val Asp Ser
            100                 105                 110

Gly Leu Tyr Leu Gly Met Asn Glu Lys Gly Glu Leu Tyr Gly Ser Glu
        115                 120                 125

Lys Leu Thr Gln Glu Cys Val Phe Arg Glu Gln Phe Glu Glu Asn Trp
    130                 135                 140

Tyr Asn Thr Tyr Ser Ser Asn Leu Tyr Lys His Val Asp Thr Gly Arg
145                 150                 155                 160

Arg Tyr Tyr Val Ala Leu Asn Lys Asp Gly Thr Pro Arg Glu Gly Thr
                165                 170                 175

Arg Thr Lys Arg His Gln Lys Phe Thr His Phe Leu Pro Arg Pro Val
            180                 185                 190

Asp Pro Asp Lys Val Pro Glu Leu Tyr Lys Asp Ile Leu Ser Gln Ser
        195                 200                 205
```

<210> SEQ ID NO 2
<211> LENGTH: 208
<212> TYPE: PRT
<213> ORGANISM: Mus sp.

<400> SEQUENCE: 2

```
Met Ala Pro Leu Gly Glu Val Gly Ser Tyr Phe Gly Val Gln Asp Ala
1               5                   10                  15

Val Pro Phe Gly Asn Val Pro Val Leu Pro Val Asp Ser Pro Val Leu
            20                  25                  30

Leu Ser Asp His Leu Gly Gln Ser Glu Ala Gly Gly Leu Pro Arg Gly
        35                  40                  45

Pro Ala Val Thr Asp Leu Asp His Leu Lys Gly Ile Leu Arg Arg Arg
    50                  55                  60

Gln Leu Tyr Cys Arg Thr Gly Phe His Leu Glu Ile Phe Pro Asn Gly
65                  70                  75                  80

Thr Ile Gln Gly Thr Arg Lys Asp His Ser Arg Phe Gly Ile Leu Glu
                85                  90                  95

Phe Ile Ser Ile Ala Val Gly Leu Val Ser Ile Arg Gly Val Asp Ser
            100                 105                 110

Gly Leu Tyr Leu Gly Met Asn Glu Lys Gly Glu Leu Tyr Gly Ser Glu
        115                 120                 125

Lys Leu Thr Gln Glu Cys Val Phe Arg Glu Gln Phe Glu Glu Asn Trp
    130                 135                 140

Tyr Asn Thr Tyr Ser Ser Asn Leu Tyr Lys His Val Asp Thr Gly Arg
```

```
                145                 150                 155                 160
Arg Tyr Tyr Val Ala Leu Asn Lys Asp Gly Thr Pro Arg Glu Gly Thr
                165                 170                 175

Arg Thr Lys Arg His Gln Lys Phe Thr His Phe Leu Pro Arg Pro Val
                180                 185                 190

Asp Pro Asp Lys Val Pro Glu Leu Tyr Lys Asp Ile Leu Ser Gln Ser
                195                 200                 205

<210> SEQ ID NO 3
<211> LENGTH: 208
<212> TYPE: PRT
<213> ORGANISM: Rattus norvegicus

<400> SEQUENCE: 3

Met Ala Pro Leu Gly Glu Val Gly Ser Tyr Phe Gly Val Gln Asp Ala
1               5                   10                  15

Val Pro Phe Gly Asn Val Pro Val Leu Pro Val Asp Ser Pro Val Leu
                20                  25                  30

Leu Ser Asp His Leu Gly Gln Ser Glu Ala Gly Gly Leu Pro Arg Gly
                35                  40                  45

Pro Ala Val Thr Asp Leu Asp His Leu Lys Gly Ile Leu Arg Arg Arg
        50                  55                  60

Gln Leu Tyr Cys Arg Thr Gly Phe His Leu Glu Ile Phe Pro Asn Gly
65                  70                  75                  80

Thr Ile Gln Gly Thr Arg Lys Asp His Ser Arg Phe Gly Ile Leu Glu
                85                  90                  95

Phe Ile Ser Ile Ala Val Gly Leu Val Ser Ile Arg Gly Val Asp Ser
                100                 105                 110

Gly Leu Tyr Leu Gly Met Asn Glu Lys Gly Glu Leu Tyr Gly Ser Glu
                115                 120                 125

Lys Leu Thr Gln Glu Cys Val Phe Arg Glu Gln Phe Glu Glu Asn Trp
        130                 135                 140

Tyr Asn Thr Tyr Ser Ser Asn Leu Tyr Lys His Val Asp Thr Gly Arg
145                 150                 155                 160

Arg Tyr Tyr Val Ala Leu Asn Lys Asp Gly Thr Pro Arg Glu Gly Thr
                165                 170                 175

Arg Thr Lys Arg His Gln Lys Phe Thr His Phe Leu Pro Arg Pro Val
                180                 185                 190

Asp Pro Asp Lys Val Pro Glu Leu Tyr Lys Asp Ile Leu Ser Gln Ser
                195                 200                 205

<210> SEQ ID NO 4
<211> LENGTH: 208
<212> TYPE: PRT
<213> ORGANISM: Sus scrofa

<400> SEQUENCE: 4

Met Ala Pro Leu Gly Glu Val Gly Asn Tyr Phe Gly Val Gln Asp Ala
1               5                   10                  15

Val Pro Phe Gly Asn Val Pro Val Leu Pro Val Asp Ser Pro Val Leu
                20                  25                  30

Leu Ser Asp His Leu Ser Gln Ser Glu Ala Gly Gly Leu Pro Arg Gly
                35                  40                  45

Pro Ala Val Thr Asp Leu Asp His Leu Lys Gly Ile Leu Arg Arg Arg
        50                  55                  60

Gln Leu Tyr Cys Arg Thr Gly Phe His Leu Glu Ile Phe Pro Asn Gly
65                  70                  75                  80
```

```
Thr Ile Gln Gly Thr Arg Lys Asp His Ser Arg Phe Gly Ile Leu Glu
                85                  90                  95
Phe Ile Ser Ile Ala Val Gly Leu Val Ser Ile Arg Gly Val Asp Ser
            100                 105                 110
Gly Leu Tyr Leu Gly Met Asn Glu Lys Gly Glu Leu Tyr Gly Ser Glu
        115                 120                 125
Lys Leu Thr Gln Glu Cys Val Phe Arg Glu Gln Phe Glu Glu Asn Trp
    130                 135                 140
Tyr Asn Thr Tyr Ser Ser Asn Leu Tyr Lys His Val Asp Thr Gly Arg
145                 150                 155                 160
Arg Phe Tyr Val Ala Leu Asn Lys Asp Gly Thr Pro Arg Glu Gly Thr
                165                 170                 175
Arg Thr Lys Arg His Gln Lys Phe Thr His Phe Leu Pro Arg Pro Val
            180                 185                 190
Asp Pro Asp Lys Val Pro Glu Leu Tyr Lys Asp Ile Leu Ser Gln Ser
        195                 200                 205
```

FGF-9 AND ITS USE RELATING TO BLOOD VESSELS

This application is the National Stage of International Application No. PCT/CA2009/000586 filed on May 1, 2009, which claims the benefit of U.S. Provisional Application No. 61/050,143 filed May 2, 2008. The disclosures of the above referenced applications are fully incorporated by reference.

FIELD OF THE INVENTION

The present invention relates to controlling formation and/or stabilization of blood vessels. More particularly, the present invention relates to use of a FGF-9 molecule for controlling formation and/or stabilization of blood vessels

BACKGROUND OF THE INVENTION

The development of new blood vessels (angiogenesis) is fundamental not only during embryogenesis but also as a protective response in adult tissue subjected to ischemia. To be productive, the formation of endothelial lined vessels is typically followed by the recruitment of perivascular cells. This maturation process produces functional vessels which persist over time and are responsive to physiological stimuli. The production of mature vessels is of therapeutic importance in the treatment of ischemic disease. However, there has been little success in stimulating the formation of mature microvessels in adults.

Angiogenesis is a physiological process involving the growth of new blood vessels from pre-existing vessels. Angiogenesis entails the proliferation and migration of endothelial cells to form immature vascular networks. There is also a maturation phase of angiogenesis that entails the recruitment of mesenchymal cells, including pericytes and/or smooth muscle cells (SMCs), which wrap the newly formed vessels to stabilize them. This is referred to as angiogenic maturation. Such angiogenic maturation may be the process of a recent angiogenic event, or include maturation, maintenance, and stabilization of vessels generated through angiogenesis at any point in development and post-natally. Angiogenic maturation may also include the process of maturation, supporting, and stabilizing of blood vessels generated through the process of vasculogenesis as defined by the de novo condensation of appropriate stem, progenitor, or more differentiated cell types into tubular vessels.

A number of proteins, typically referred to as angiogenic proteins, are known to promote angiogenesis. Such angiogenic proteins include members of the fibroblast growth factor (FGF) family, the vascular endothelial growth factor (VEGF) family, the platelet-derived growth factor (PDGF) family, or the insulin-like growth factor (IGF) family. For example, certain FGF and VEGF family members have been recognized as regulators of angiogenesis during growth and development. Their role in promoting angiogenesis in adult animals has also been examined.

Angiogenic proteins, such as FGF family members, have been disclosed in many patent documents, for example U.S. Pat. No. 4,956,455 (titled Bovine fibroblast growth factor, issued Sep. 11, 1990), U.S. Pat. No. 5,155,214 (titled Basic fibroblast growth factor, issued Oct. 13, 1992), U.S. Pat. No. 5,302,702 (titled Chimeric fibroblast growth factors, issued Apr. 12, 1994), U.S. Pat. No. 5,314,872 (titled: Glucan sulfate, stabilized fibroblast growth factor composition, issued May 24, 1994), U.S. Pat. No. 5,352,589 (titled Deletion mutant of basic fibroblast growth factor and production thereof, issued Oct. 4, 1994), U.S. Pat. No. 5,371,206 (titled DNA encoding chimeric fibroblast growth factors, issued Dec. 6, 1994), U.S. Pat. No. 5,387,673 (titled Active fragments of fibroblast growth factor, issued Feb. 7, 1995), U.S. Pat. No. 5,439,818 (titled DNA encoding human recombinant basic fibroblast growth factor, issued Aug. 8, 1995), U.S. Pat. No. 5,491,220 (titled Surface loop structural analogues of fibroblast growth factors, issued Feb. 13, 1996), U.S. Pat. No. 5,514,566 (titled Methods of producing recombinant fibroblast growth factors, issued May 7, 1996), U.S. Pat. No. 5,604,293 (titled Recombinant human basic fibroblast growth factor, issued Feb. 18, 1997).

The fibroblast growth factors (FGF) are a family of at least twenty-three structurally related polypeptides (named FGF1 to FGF23) that are characterized by a high degree of affinity for proteoglycans, such as heparin. The various FGF molecules range in size from 15-23 kD, and exhibit a broad range of biological activities in normal and malignant conditions. Activities that have been characterized for FGF molecules include nerve cell adhesion and differentiation; wound healing; as mitogens toward many mesodermal and ectodermal cell types, as trophic factors, as differentiation inducing or inhibiting factors; and as an angiogenic factor. For example, PCT Publication WO98/50079 (titled Techniques And Compositions For Treating Heart Failure And Ventricular Remodeling By in Vivo Delivery Of Angiogenic Transgenes, published Dec. 30, 2004) describes the use of FGF2, FGF4, or FGF5 to ameliorate regional myocardial contractile dysfunction in an animal model of heart failure. The therapeutic mechanism of action is stated to be angiogenesis.

Angiogenesis entails the proliferation and migration of endothelial cells from the existing vasculature in order to create new blood vessels. These nascent vessels are incomplete as they lack supporting layers of mature smooth muscle cells (SMCs). As a result, immature vascular beds are prone to regression due to the fact that endothelial cells retract and eventually undergo apoptosis. Stabilization of newly or previously formed blood vessels through angiogenic maturation by SMCs both prevents regression while also conferring the critical ability to regulate blood pressure. While a number of factors that stimulate the recruitment of SMCs to blood vessels during development have been identified, these pathways are poorly understood with respect to postnatal angiogensis.

Currently, blood vessel formation stimulated by established soluble angiogenic cytokines either in vivo or simulated in vitro are short-lived due to the fact that they lack complete layers of supporting SMCs and are therefore of limited therapeutic or experimental value.

SUMMARY OF THE INVENTION

The invention provides compositions and methods to promote angiogenesis maturation and stabilization. It is herein first demonstrated that compositions comprising FGF-9 and one or more other angiogenic polypeptides can be used in vitro and in vivo to promote, control and stabilize blood vessel formation. This includes the improvement of blood vessel condition of existing blood vessels. As such, the invention has wide application and utility as a culture supplement for in vitro culture of cells and/or tissues. The invention also has wide therapeutic application in clinical conditions where angiogenesis is required or is beneficial to provide stabilized blood vessels. In any of the embodiments of the invention the invention can be provided a composition for systemic or local administration with or without a carrier or carrier matrix.

According to an aspect of the present invention there is provided a method of promoting blood vessel formation in hypoxic or ischemic tissues in a patient in need thereof, comprising contacting said tissue with a composition comprising FGF-9 polypeptide and one or more other isolated angiogenic polypeptide.

According to another aspect of the present invention is a method of treating a condition amenable to treatment by promoting angiogenesis, said method comprising administering to a subject in need thereof an amount of a FGF-9 polypeptide composition comprising FGF-9 and one or more other angiogenic polypeptides, effective for promoting angiogenesis in said subject.

According to a further aspect of the present invention is a method for improving the condition of a blood vessel, such improvement comprising the proliferation and migration of endothelial cells to form immature vascular networks, and the recruitment of mesenchymal cells, including pericytes and/or smooth muscle cells (SMCs) to wrap the vessels to stabilize them and thus improve their condition, the method comprising contacting the blood vessel with a composition comprising FGF-9 and one or more other angiogenic factor(s).

In an aspect, there is provided a composition for controlling formation and/or stabilization of a blood vessel comprising a first isolated nucleic acid molecule that encodes a FGF-9 polypeptide and optionally a second isolated nucleic acid molecule that encodes another angiogenic polypeptide. In aspects, the nucleic acid molecule can be DNA, RNA, single or double-stranded.

In another aspect, there is provided a composition for controlling formation and/or stabilization of a blood vessel comprising an isolated FGF-9 polypeptide and optionally one or more other angiogenic polypeptides.

In another aspect, there is provided a composition for stabilizing existing blood vessels in need of such treatment, the composition comprising an isolated FGF-9 polypeptide and one or more angiogenic polypeptides.

In yet another aspect, there is provided a composition for controlling formation and/or stabilization of a blood vessel comprising a recombinant cell producing an isolated FGF-9 polypeptide and optionally another isolated angiogenic polypeptide.

In a further aspect, there is provided a composition for promoting therapeutic angiogenesis in an animal comprising a first isolated nucleic acid molecule that encodes a FGF-9 polypeptide and a second isolated nucleic acid molecule that encodes an angiogenic polypeptide.

In still a further aspect, there is provided a composition for promoting therapeutic angiogenesis in an animal comprising an isolated FGF-9 polypeptide and another angiogenic polypeptide.

In an even further aspect, there is provided a composition for promoting therapeutic angiogenesis in an animal comprising a recombinant cell producing an isolated FGF-9 polypeptide and another isolated angiogenic polypeptide.

In another aspect, there is provided a method of promoting formation of mature blood vessels in a subject comprising administering an effective amount of FGF-9 to the subject.

In still another aspect, there is provided a method of treating ischemia in a subject comprising administering an effective amount of FGF-9 to the subject.

In yet another aspect, there is provided a use of FGF-9 for preparation of a medicament.

In still yet another aspect, there is provided a use of FGF-9 for preparation of a medicament for promoting formation of mature blood vessels in a subject or improving the condition of an existing blood vessel In another aspect, there is provided a use of FGF-9 for preparation of a medicament for treating ischemia in a subject.

In even another aspect, there is provided a use of FGF-9 for promoting formation of mature blood vessels in a subject.

In still another aspect, there is provided a use of FGF-9 for treating ischemia in a subject.

In a further aspect, there is provided a kit comprising FGF-9 and a matrix material, and instructions for preparing an in vitro vasculogenesis assay.

In accordance with a further aspect, there is provided a kit comprising a FGF-9 containing composition and a matrix material, with instructions for use and for preparing an in vitro angiogenesis assay.

In still a further aspect, there is provided an in vitro vasculogenesis assay comprising a matrix material, FGF-9, endothelial cells, smooth muscle cells, and a matrix material for supporting growth and proliferation of cells.

In yet a further aspect, there is provided a use of FGF-9 for stabilization of blood vessels in vitro or in vivo.

In yet a further aspect of the invention, there is provided a FGF-9 containing composition for the promotion of the angiogenenic maturation of blood vessels in vitro or in vivo.

In another aspect, there is provided a use of FGF-9 for treatment of cancer.

Other features and advantages of the present invention will become apparent from the following detailed description. It should be understood, however, that the detailed description and the specific examples while indicating embodiments of the invention are given by way of illustration only, since various changes and modifications within the spirit and scope of the invention will become apparent to those skilled in the art from said detailed description.

BRIEF DESCRIPTION OF THE DRAWINGS

The present invention will become more fully understood from the detailed description given herein and from the accompanying drawings, which are given by way of illustration only and do not limit the intended scope of the invention as herein described in its various embodiments.

FIG. 1 shows mRNA coding region sequence and corresponding amino acid sequence for mammalian FGF-9A) *Homo sapiens* (NCBI gi:391718), B) *Mus musculus* (NCBI gi:1161346), C) *Rattus norvegicus* (NCBI gi:391852);

FIG. 2 shows a multiple sequence alignment of Human, Mouse, Rat, and Pig FGF-9 amino acid sequences;

FIG. 3 shows steps in a high throughput screen for factors secreted by SMCs as they acquire specialized functions;

FIG. 4 shows that FGF-9 is upregulated as SMCs acquired specialized functions;

FIG. 12 shows that FGF-9 stabilizes the neovasculature;

DETAILED DESCRIPTION OF THE EMBODIMENTS

Figure 5:
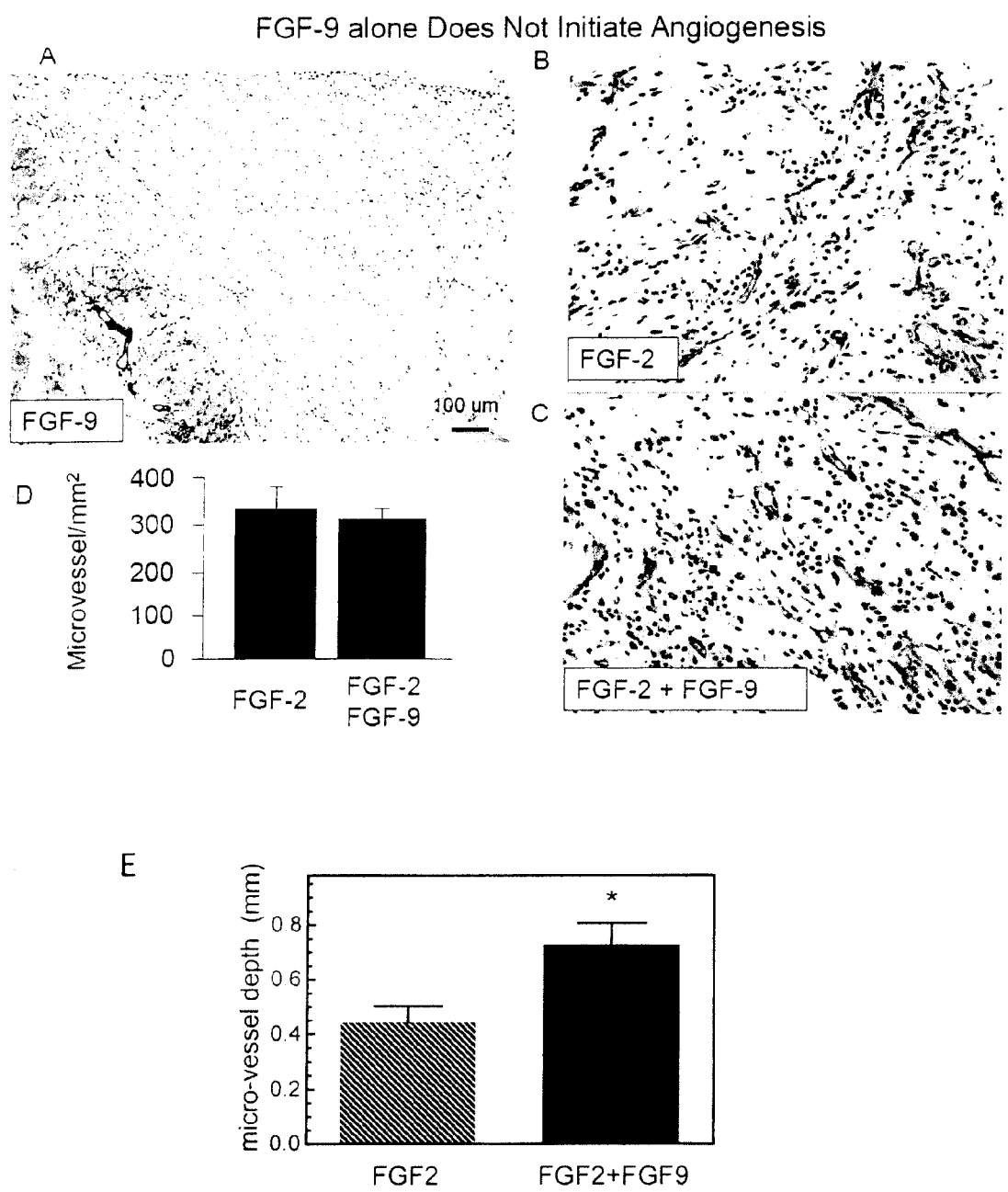
FIG. 5 shows that FGF-9 does not initiate the angiogenic process in subcutaneously implanted matrigel in mice.

For convenience, before further description of the present invention, certain terms employed in the specification, examples, and appended claims are provided herein. These definitions should be read in light of the remainder of the disclosure and understood as by a person of skill in the art. Also, the terms "including" (and variants thereof), "such as", "e.g." as used herein are non-limiting and are for illustrative purposes only. The articles "a" and "an" are used herein to refer to one or to more than one (i.e. to at least one) of the grammatical object of the article. By way of example, "an element" means one element or more than one element. The term "angiogenesis" is an art-recognized term, and refers to the process and creation of new blood vessels formed from pre-existing blood vessels. The term "restenosis" refers to a re-narrowing of a blood vessel, thereby restricting blood flow. This re-narrowing can be caused by, for example, a vessel's response to an injury inflicted during balloon angioplasty. The term "hypoxic tissue" refers to tissue with an insufficient amount of oxygen. The term "ischemic tissue" refers to tissue with insufficient blood flow.

All publications and patents mentioned herein, including those items listed below, are hereby incorporated by reference in their entirety as if each individual publication or patent was specifically and individually indicated to be incorporated by reference.

Methods and compositions for controlling formation and/or stabilization of blood vessels are described herein. More specifically, methods and compositions for controlling angiogenesis and/or vasculogenesis are described herein.

Angiogenesis is a physiological process involving the growth of new blood vessels from pre-existing vessels. One aspect of angiogenesis entails the proliferation and migration of endothelial cells to form immature vascular networks. Another aspect of angiogenesis is a maturation phase that entails the recruitment of mesenchymal cells, including pericytes and/or smooth muscle cells (SMCs) that wrap vessels to stabilize them. This is referred to as angiogenic maturation. Such angiogenic maturation may be the process of a recent angiogenic event, or include maturation, maintenance, and stabilization of vessels generated through angiogenesis at any point in development and post-natally. Thus, angiogenic maturation may occur independently of the aspect of angiogenesis pertaining to formation of nascent or immature blood vessels, and therefore may be beneficial in stabilizing any blood vessel, nascent or otherwise. For example, existing blood vessels in an adult animal that exhibit vascular leakage, or are at risk of exhibiting vascular leakage, can be stabilized by the process of angiogenic maturation. Angiogenic maturation may also include the process of maturation, supporting, and stabilizing of blood vessels generated through the process of vasculogenesis in vitro and/or in vivo. Vasculogenesis comprises de novo condensation of appropriate stem, progenitor, or more differentiated cell types into tubular vessels.

An angiogenic molecule is meant to encompass nucleic acids, polypeptides, small molecule chemical compounds or any other molecule that can be used to control at least one aspect of angiogenesis. For example, an angiogenic polypeptide is a polypeptide that can be used to control at least one aspect of angiogenesis. Angiogenic polypeptides have been identified from many naturally occurring sources and variants thereof have also been produced and characterized. Such angiogenic polypeptides include members of the fibroblast growth factor (FGF) family (for example FGF-1, FGF-2, FGF-4, FGF-5, FGF-6, or FGF-9), the vascular endothelial growth factor (VEGF) family (for example VEGF-121, VEGF-145, VEGF-165, VEGF-167, VEGF-186, VEGF-189, VEGF-206, or VEGF-C), the platelet-derived growth factor (PDGF) family (for example PDGF-α or PDGF-β), or the insulin-like growth factor (IGF) family. Other non-limiting examples of angiogenic peptides include PIGF, Hedgehog family member (Sonic, Indian and Desert), and SDF-1.

Angiogenic molecules may be used to prepare compositions that are useful for controlling at least one aspect of angiogenesis. Such compositions may be useful in any method, in vivo or in vitro, where formation and/or stabilization of a blood vessel is desired. Stabilization of blood vessels may be useful in forming or maintaining blood vessels, for example, by reducing regression of newly formed vessels, maintaining or conferring responsiveness to vasoactive stimuli, reduction of vascular leakage or formation of tight junctions. Stabilization of blood vessels may be useful in respect of both angiogenesis or vasculogenesis.

Compositions and methods described herein will comprise a FGF molecule, and more typically a FGF polypeptide.

In one example, compositions comprising a FGF-9 molecule are provided.

Without wishing to be bound by theory, FGF-9 is believed to control stabilization and/or formation of blood vessels or control angiogenesis and/or vasculogenesis by influencing migration of mesenchymal cells to blood vessels. The mesenchymal cells can provide stability to a blood vessel by physical contact and more specifically by circumferential wrapping of blood vessels. The blood vessels may be nascent or may be at any level of development or maturity.

Compositions comprising a FGF-9 molecule may be useful to control angiogenesis. Compositions comprising a FGF-9 molecule may be useful to promote maturation of blood vessels during angiogenesis. Compositions comprising a FGF-9 molecule may also be useful to promote formation of functional blood vessels during angiogenesis. Compositions comprising a FGF-9 molecule may also be useful for recruitment of smooth muscle alpha-actin positive cells to nascent blood vessels during angiogenesis. Compositions comprising a FGF-9 molecule may also be useful for inducing expression of smooth muscle alpha-actin in mural cell precursors. Compositions comprising a FGF-9 molecule may also be useful to promote the formation and/or maturation and/or stabilization of functional blood vessels during vasculogenesis including stimulation of re-innervation of blood vessels. Compositions comprising a FGF-9 molecule may also be useful for therapeutic angiogenesis, for example in treatment of ischemia by stimulating creation of new functional blood vessels in ischemic organs, tissues or parts to increase the level of oxygen-rich blood reaching these areas.

Compositions comprising a FGF-9 molecule may be used to treat any disease or condition where the formation of new blood vessels provides a prophylactic and/or therapeutic benefit in absence of existing extracellular structure. Accordingly, a method for controlling angiogenesis in a subject comprises administering a composition comprising a FGF-9 molecule and another angiogenic agent in combination with a natural or synthetic or natural-synthetic combination of extracellular matrix as a therapeutic biomaterial. The FGF-9 molecule may be administered systemically or locally in a region where therapeutic angiogenesis is needed to facilitate angiogenesis within the appropriate extracellular structure as would be required for therapeutic tissue engineering.

Compositions comprising a FGF-9 molecule may be used to treat any disease or condition where the formation of new blood vessels provides a prophylactic and/or therapeutic benefit. Accordingly, a method for controlling angiogenesis in a subject comprises administering a composition comprising a FGF-9 molecule. In another example, a method for treating ischemia in a subject comprises administering a composition comprising a FGF-9 molecule. The FGF-9 molecule may be administered systemically or locally in a region where therapeutic angiogenesis is needed to treat ischemia.

Ischemia can be described as an inadequate flow of blood to a part of the body, caused by constriction or blockage of the blood vessels supplying it, with resultant damage or dysfunction to this part of the body. Ischemia is a well known feature of heart diseases, transient ischemic attacks, cerebrovascular accidents, ruptured arteriovenous malformations, and peripheral artery occlusive disease. The heart, the kidneys, and the brain are among the organs that are the most sensitive to inadequate blood supply. Ischemia in brain tissue, for example due to stroke or head injury, causes a process called the ischemic cascade to be unleashed, in which proteolytic enzymes, reactive oxygen species, and other harmful chemicals damage and may ultimately kill brain tissue. Ischemia to the heart can cause angina (CIP), which is sometimes debilitating and refractory to current forms of therapy. Ischemia to the heart can also lead to heart muscle injury and muscle death (myocardial infarction).

Ischemia to the lower limbs is also common in diabetes and can cause refractory lower limb pain (claudication) and lead to gangrene and amputation.

Compositions comprising a FGF-9 molecule may be used to treat any disease or condition where the stabilization or angiogenic maturation of existing blood vessels provides a prophylactic and/or therapeutic benefit. Accordingly, a method for controlling angiogenesis in a subject comprises administering a composition comprising a FGF-9 molecule. In another example, a method for treating vascular leakage in a subject comprises administering a composition comprising a FGF-9 molecule. The FGF-9 molecule may be administered systemically or locally in a region where therapeutic angiogenic maturation is needed to treat or mitigate risk in a patient.

Vascular leakage can be described as the unregulated movement of molecules, such as proteins, toxins, and oxidized molecules, out of the blood to the nearby tissues. This leakage can lead to the damage and death of local cells. This is a prominent feature of diabetic retinopathy, which can lead to blindness. It may also be a feature of neurological disorders such as Lou Gehrig's disease and Alzheimer's disease. When severe vascular leakage is accompanied by extravasation of red blood cells and other circulating cells. This is referred to as hemorrhage. Hemorrhage from small vessels can have severe consequences for tissues such as the brain and the eye.

In a further embodiment of the invention, the compositions as described herein have utility in the field of cancer for the treatment thereof. The administration of FGF-9 compositions of the invention may be used for stabilizing angiogenesis in tumours and effectively causing a localization of the cancer and less metastases such that the tumour can be more readily excised from the patient. In this aspect, the tumour may be directly targeted with local administration of the FGF-9 containing compositions of the invention. Alternatively, the FGF-9 containing compositions of the invention may be administered systemically and/or locally for reduction in mestastases of cancerous cells throughout the body. It is expected that tumours so treated will be more readily excisable from the patient with less chance of tumour metastases.

Compositions comprising a FGF-9 molecule and another angiogenic molecule may be used in combination with vascular endothelial cells and vascular smooth muscle cells with or without appropriate other cell types to generate individual, a system, or a network of stabilized blood vessels in vitro. In such cases, the existence of stabilized blood vessels would be of benefit for research and development purposes, evaluation of potential therapeutic compounds, or in assessing the activity of modified cells in blood vessel formation or angiogenesis for experimental purposes. Accordingly, a method for controlling angiogenesis in vitro comprises administering a composition comprising a FGF-9 molecule and another angiogenic molecule in a range of concentrations appropriate for inducing vessel formation and maturation with a suitable culture medium.

In another non-limiting example, such a method for generating stabilized blood vessels in vitro for the described purposes may benefit from the formation of 3-dimensional structures. Accordingly, for the generation of such 3 dimensional vascular structures such culture medium may include a composition of FGF-9 and another angiogenic molecule at an appropriate concentration to generate stabilized blood vessels; an extracellular matrix that may include but are not limited to such factors as fibrin, Matrigel, collagen, hyaluronic acid, proteoglycans, derivatives thereof or synthetic structural agents; and may or may not contain a natural or synthetic cross linking agent to generate the three dimensional structure.

Without wishing to be limited by theory, FGF-9 molecules appear to promote formation of functional blood vessels by influencing a contractile phenotype in smooth muscle cells and stimulating their recruitment to nacsent blood vessels. A fundamental characteristic of vascular smooth muscle cells is their ability to convert between immature, proliferative and mature, contractile phenotypes. One process that requires this plasticity is angiogenesis where smooth muscle cells must proliferate and migrate to nascent microvessels. Smooth muscle cells must then wrap around these microvessels and reacquire the ability to contract in order to stablize the nascent vasculature. Using a unique smooth muscle cell-line that reversibly converts between immature and mature phenotypes, secreted factors that may regulate the stabilization of neovessels have been identified. High density microarray analysis of maturing smooth muscle cells revealed only 27 secreted factors were upregulated with FGF-9 being the most upregulated. In contrast other FGFs showed no change (FGF-7,-11,-12,-14,-18) or were downregulated (FGF-1,-2,-5) as smooth muscle cells matured.

Without limitation, the FGF-9 molecule may be a full-length naturally occurring polypeptide or a variant thereof, or may be a nucleic acid molecule encoding a FGF-9 polypeptide or variant thereof. Furthermore, a recombinant cell producing the FGF-9 molecule is provided.

An FGF-9 polypeptide may be provided by any source or method, for example, natural isolate or recombinant or synthetic origin or suitable combinations thereof. Administration of the FGF-9 polypeptide to a subject can be used to control angiogenesis, and more specifically to promote recruitment of smooth muscle cells during angiogenesis. The FGF-9 polypeptide may be of any length provided that its angiogenic activity is maintained. The sequence of the FGF-9 polypeptide may be based on a complete or partial naturally occurring amino acid sequence. An FGF-9 polypeptide may be used either singly or in combination with other polypeptides, angiogenic or otherwise, in the preparation of a composition that controls angiogenesis. A polypeptide refers to a chain of amino acids, for example peptides, oligopeptides, or proteins, having a biological function, and does not refer to a specific length of the chain.

An isolated FGF-9 polypeptide is a polypeptide that has been identified and separated and/or recovered from at least one component of its natural environment. The isolated polypeptide will typically have been purified by at least one purification step, and, in some embodiments purification may be achieved (1) to a degree sufficient to obtain at least 15 residues of N-terminal or internal amino acid sequence by use of a sequenator, or (2) to homogeneity by SOS-PAGE under non-reducing or reducing conditions using Coomassie blue or, preferably, silver stain. Isolated polypeptide includes polypeptide in situ within recombinant cells, since at least one component of the FGF-9 polypeptide natural environment will not be present. An isolated polypeptide may be produced by synthetic or recombinant techniques, for example as described in J. Sambrook, E. F. Fritsch, and T. Maniatis, 1989, Molecular Cloning: A Laboratory Manual, Second Edition, Books 1-3, Cold Spring Harbor Laboratory Press. An isolated polypeptide produced as a result of recombinant techniques may be referred to as a recombinant polypeptide.

A nucleic acid encoding an FGF-9 polypeptide may be any nucleic acid molecule of, for example. cDNA, genomic DNA, synthetic DNA or RNA origin or suitable combinations thereof. Administration of the nucleic acid encoding an FGF-9 polypeptide to a subject can be used to control angiogenesis, and more specifically to promote recruitment of smooth muscle cells during angiogenesis. The nucleic acid may be of any length provided that the angiogenic activity is maintained by the encoded FGF-9 polypeptide. The sequence of the nucleic acid encoding an FGF-9 polypeptide may be based on a complete or partial naturally occurring nucleic acid sequence. A nucleic acid sequence encoding an FGF-9 polypeptide may be used either singly or in combination with other nucleic acid sequences, encoding angiogenic polypeptides or encoding any other desired polypeptide, in the preparation of a composition to control angiogenesis.

An isolated nucleic acid molecule encoding a FGF-9 polypeptide is a nucleic acid molecule that is identified and separated from at least one contaminant nucleic acid molecule with which it is ordinarily associated in the natural source of the nucleic acid. Such an isolated nucleic acid molecule is other than in the form or setting in which it is found in nature. Isolated nucleic acid molecules therefore are distinguished from the nucleic acid molecule as it exists in natural cells. An isolated nucleic acid molecule encoding a FGF-9 polypeptide includes nucleic acid molecule encoding a FGF-9 polypeptide contained in cells that ordinarily express the FGF-9 polypeptide where, for example, the nucleic acid molecule is in a chromosomal or extrachromosomal location different from that of natural cells. The isolated nucleic acid molecule may be referred to as a recombinant nucleic acid molecule where the isolated nucleic acid molecule has been manipulated using recombinant techniques, for example, as described in J. Sambrook, E. F. Fritsch, and T. Maniatis, 1989, Molecular Cloning: A Laboratory Manual, Second Edition, Books 1-3, Cold Spring Harbor Laboratory Press.

Variants include, without limitation, analogs, derivatives, fragments, truncations, splice variants, mutants, deletions, substitutions, insertions, fusions and the like.

A FGF-9 polypeptide or a nucleic acid encoding a FGF-9 polypeptide may be mutated or changed or derivatised in any manner desired (for example, any number or combination of deletions, insertions, or substitutions) to produce a corresponding variant. Use of such variants in controlling angiogenesis is contemplated, and such a variant nucleic acid or variant polypeptide may be mutated or changed or derivatised in any manner in comparison to a naturally occurring nucleic acid or polypeptide sequence, respectively, provided that the angiogenic activity is maintained. Similarly, nucleic acids or polypeptides having varying degrees of sequence identity to a corresponding naturally occurring nucleic acid or polypeptide sequence may be tolerated without eliminating an angiogenic activity. For example, a composition may comprise an FGF-9 polypeptide having a sequence that is identical to a naturally-occurring form of the FGF-9 polypeptide or a variant thereof that has a sequence that is at least 80% identical to a naturally-occurring form of the FGF-9 polypeptide. As another example, a composition may comprise a nucleic acid molecule having a coding sequence that is identical to a naturally-occurring form of the coding sequence or a variant thereof that has a sequence that is at least 70% identical to a naturally-occurring form of the coding sequence. Determination of sequence identity of proteins and nucleic acids by computer based methods, as well as nucleic acid hybridization techniques using high stringency conditions for determining or identifying nucleic acid sequences that share high (eg., at least 70%) sequence identity are well known to the skilled person.

Stringency of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of sequence identity between the probe and hybridizable sequence, the higher the relative temperature which can be used. High stringency conditions may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. Hybridization and wash times should be sufficient for achieving equilibrium.

Percent (%) sequence identity of amino acid or nucleic acid sequences with respect to FGF-9 polypeptides and nucleic acid sequences encoding FGF-9 polypeptides is the percentage of residues in a candidate sequence that are identical with the FGF-9 polypeptide amino acid sequence or the FGF-9 polypeptide-encoding nucleic acid sequence, as the case may be, after aligning the sequences and introducing gaps, if necessary, to achieve the maximum percent sequence identity. Alignment for purposes of determining percent amino acid sequence identity or percent nucleic acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over a desired length of sequence, for example, at least 20, 30, 40, 50, 60, 70, 80, 90, 100, 110, 120, 130, 140, 150, 160, 170, 180, 190, or 200 residues or even the full-length of the sequences being compared.

When considering a FGF-9 polypeptide or variant thereof, the variant FGF-9 polypeptide will typically have an amino acid sequence that is at least 80, 82, 84, 86, 88, 90, 92, 94, 96, or 98 percent identical to the corresponding FGF-9 polypeptide.

When considering a nucleic acid sequence encoding a FGF-9 polypeptide or variant thereof, the variant nucleic acid sequence will typically be at least 70, 72, 74, 76, 78, 80, 82, 84, 86, 88, 90, 92, 94, 96, or 98 percent identical to the corresponding nucleic acid encoding the FGF-9 polypeptide.

Techniques and strategies for producing variants are well known in the art. In one example, with regard to polypeptides, a FGF-9 polypeptide may be modified in vivo or in vitro by, glycosylation, amidation, phosphorylation, carboxylation, truncation, fragmentation, substitution, and the like without eliminating angiogenic activity. In another example, with regard to nucleic acids, substitution mutations can be made in a nucleic acid encoding a FGF-9 polypeptide such that a particular codon is changed to a codon which codes for a different amino acid. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e. by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. Groupings of amino acids are known to the skilled person. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charges (basic) amino acids include arginine, lysine and histidine. The negatively charged (acidic) amino acids include aspartic acid and glutamic acid. Any number of such substitutions or any other type of alteration (eg., deletion or insertion) or modification may be tolerated provided that the angiogenic effect is not eliminated.

Recombinant cells, comprising a FGF-9 polypeptide or a nucleic acid sequence that encodes a FGF-9 polypeptide may be used for controlling angiogenesis. Recombinant cell types may include any cell type that is compatible with the physiology of an intended subject for therapeutic angiogenesis or for the application of generating in vitro models of angiogenesis, vasculogenesis, or any other in vitro model employing intact and stabilized blood vessels.

A cell may be altered or modified to comprise a nucleic acid sequence that does not naturally occur in the cell, and as such the cell will be considered recombinant. In other examples, a cell may be altered or modified to comprise an additional copy of a nucleic acid sequence that naturally occurs in the cell, and such cells will also be considered recombinant. As is understood by one of skill in the art, a nucleic acid encoding a FGF-9 polypeptide may be introduced into a cell using any known technique, for example, microinjection, electroporation, viral transfection, lipofectamine transfection, calcium phosphate precipitation and the like. In certain non-limiting examples, a stem cell may be modified by introduction of a nucleic acid molecule encoding a FGF-9 polypeptide, and then the modified cells may be administered to a subject. In certain other examples, a nucleic acid molecule encoding a FGF-9 polypeptide may be incorporated into an appropriate construct or vehicle, for example a viral construct, and administered to a subject such that the nucleic acid molecule encoding the FGF-9 polypeptide is introduced and expressed in at least a portion of the cells of the subject.

A nucleic acid encoding a FGF-9 polypeptide may be operably linked to control sequences, typically in the context of a suitable vector. A useful control sequence may be any nucleic acid element that is necessary or advantageous for expression of the coding sequence of the nucleic acid sequence. Each control sequence may be native or foreign to the nucleic acid sequence encoding the FGF-9 polypeptide. Such control sequences include, but are not limited to, a leader, a polyadenylation sequence, a propeptide sequence, a promoter, a signal sequence, or a transcription terminator. Alternatives for incorporating control sequences are readily available to the skilled person. For example, a nucleic acid encoding a FGF-9 polypeptide may be under the control of an endogenous upstream promoter, or it may be put under control of a heterologous upstream promoter. Examples of suitable promoters for directing the transcription of the modified nucleotide sequence, such as PS4 nucleic acids, in a bacterial host include the promoter of the lac operon of *E. coli*, the *Streptomyces coelicolor* agarase gene dagA promoters, the promoters of the *Bacillus licheniformis* alpha-amylase gene (amyl), the promoters of the *Bacillus stearothermophilus* maltogenic amylase gene (amyM), the promoters of the *Bacillus amyloliquefaciens* alpha-amylase gene (amyQ), the promoters of the *Bacillus subtilis* xylA and xylB genes, the promoter of the *Bacillus subtilis* aprE gene and a promoter derived from a *Lactococcus* sp.—derived promoter including the P170 promoter. When the gene encoding the PS4 variant polypeptide is expressed in a bacterial species such as *E. coli*, a suitable promoter can be selected, for example, from a bacteriophage promoter including a T7 promoter and a phage lambda promoter.

For transcription in a fungal species, examples of useful promoters are those derived from the genes encoding the, *Aspergillus oryzae* TAKA amylase, *Rhizomucor miehei* aspartic proteinase, *Aspergillus niger* neutral alpha-amylase, *A. niger* acid stable alpha-amylase, *A. niger* glucoamylase, *Rhizomucor miehei* lipase, *Aspergillus oryzae* alkaline protease, *Aspergillus oryzae* triose phosphate isomerase or *Aspergillus nidulans* acetamidase.

Examples of suitable promoters for the expression in a yeast species include but are not limited to the Gal 1 and Gal 10 promoters of *Saccharomyces cerevisiae* and the *Pichia pastoris* AOX1 or AOX2 promoters.

Still further suitable promoters are available to the skilled person, for example, cytomegalovirus, Rous Sarcoma Virus, synthetic pox viral promoter, pox synthetic late promoter 1, pox synthetic late promoter 2 early promoter 2, pox 01L promoter, pox 14L promoter, pox 13L promoter; pox 12L promoter, pox IIL promoter, pox DIOR promoter, PRV gX, HSV-1 alpha 4, chicken beta-actin promoter, HCMV immediate early, MDV gA, MDV gB, MDV gD, ILT gB, BHV-1.1 VP8 and ILT gD and internal ribosomal entry site promoter.

A suitable vector may be any vector (for example, a plasmid or virus) which can incorporate a nucleic acid sequence encoding a FGF-9 polypeptide and any desired control sequences and can bring about the expression of the nucleic acid sequence. The choice of the vector will typically depend on the compatibility of the vector with a host cell into which the vector is to be introduced. In certain examples, the vector may exist as an extrachromosomal entity, with replication being independent of chromosomal replication, for example, a plasmid, an extrachromosomal element, a minichromosome, or an artificial chromosome. In other examples, the vector may be one which, when introduced into the host cell, is integrated into the genome and replicated together with the chromosome(s) into which it has been integrated. Still other examples of vectors and techniques for manipulating vectors will be known and apparent to the skilled person.

Recombinant cells may comprise a FGF-9 polypeptide or a nucleic acid sequence encoding a FGF-9 polypeptide, either singly or in combination, with other desired polypeptide or nucleic acid molecules, respectively, for example to optimize or enhance efficacy. Furthermore, a nucleic acid sequence may be mutated or altered prior to introduction into the cells as desired, for example for codon optimization for expression in a particular cell type. In addition, a nucleic acid sequence may be altered to encoded a fusion of a FGF-9 polypeptide with one or more other polypeptide as desired in an application, for example fusion with a targeting polypeptide or a carrier polypeptide.

The skilled person will recognize that variants described herein with respect FGF-9 molecules and cells comprising FGF-9 molecules can apply equally to other polypeptides, nucleic acid molecules, and cells that are used in combination with FGF-9 molecules and cells comprising FGF-9 molecules. In certain examples, angiogenic polypeptides, nucleic acid molecules encoding angiogenic polypeptides or cells producing angiogenic polypeptides may be used in combination with FGF-9 molecules or cells producing FGF-9 molecules. Such angiogenic polypeptides include other members of the fibroblast growth factor (FGF) family, the vascular endothelial growth factor (VEGF) family, the platelet-derived growth factor (PDGF) family, or the insulin-like growth factor (IGF) family. In certain examples, an FGF-9 molecule is used in combination with FGF2. In certain examples other polypeptides, nucleic acid molecules, or cells that are used in combination with FGF-9 molecules and cells comprising FGF-9 molecules may include appropriate extracellular matrix proteins to comprise a 3-dimensional structure in vitro or a biomaterial for therapeutic purposes. Such extracellular matrix proteins may include but are not limited to naturally occurring molecules such as collagen, fibrin, and proteoglycans.

As is understood by the skilled person, administration of polypeptides, nucleic acid molecules, or cells can be done in a variety of manners and combinations thereof. For example, administration may be done intramuscularly, subcutaneously, intravenously, intranasally, intradermaly, intrabursally, in ovo, ocularly, orally, intra-tracheally or intra-bronchially, as well as combinations of such modalities. The dose may vary with the size of the intended subject. Methods of administration are known to the skilled person, for example, U.S. Pat. Nos. 5,693,622; 5,589,466; 5,580,859; and 5,566,064. The amounts of polypeptide, nucleic acid sequence, or recombinant cell needed for preparation of a composition is well understood by one of skill in the art.

The polypeptides, nucleic acids, or recombinant cells as described herein, may be used in combination with a pharmaceutically acceptable carrier for preparation of a composition for controlling angiogenesis. Pharmaceutically acceptable carriers are well known to those skilled in the art and include but are not limited to proteins, sugars, and the like. One example of such a suitable carrier is a physiologically balanced culture medium containing one or more stabilizing agents such as hydrolyzed proteins, lactose, and the like. Another example of an acceptable carrier is 0.01-0.1M, and preferably 0.05M, phosphate buffer or 0.8% saline. Acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Examples of aqueous carriers are water, alcoholic/aqueous solutions, emulsions or suspensions, including saline and buffered media. Preservatives and other additives for pharmaceutical compositions are also well known to the skilled person, for example antimicrobials, antioxidants, chelating agents, inert gases, organic acids and the like. Another example of such a suitable carrier is a biomaterial comprising natural or synthetic extracellular matrix material.

The phrases "parenteral administration" and "administered parenterally" are art-recognized terms, and include modes of administration other than enteral and topical administration, such as injections, and include, without limitation, intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrasternal injection and infusion.

The term "treating" is an art-recognized term which includes curing as well as ameliorating at least one symptom of any condition or disease.

The phrase "pharmaceutically acceptable" is art-recognized. In certain embodiments, the term includes compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" is art-recognized, and includes, for example, pharmaceutically acceptable materials, compositions or vehicles, such as a liquid or solid filler, diluent, excipient, solvent or encapsulating material, involved in carrying or transporting any subject composition from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically acceptable salts" is art-recognized, and includes relatively non-toxic, inorganic and organic acid addition salts of compositions of the present invention, including without limitation, therapeutic agents, excipients, other materials and the like. Examples of pharmaceutically acceptable salts include those derived from mineral acids, such as hydrochloric acid and sulfuric acid, and those derived from organic acids, such as ethanesulfonic acid, benzenesulfonic acid, p-toluenesulfonic acid, and the like. Examples of suitable inorganic bases for the formation of salts include the hydroxides, carbonates, and bicarbonates of ammonia, sodium, lithium, potassium, calcium, magnesium, aluminum, zinc and the like. Salts may also be formed with suitable organic bases, including those that are non-toxic and strong enough to form such salts. For purposes of illustration, the class of such organic bases may include mono-, di-, and trialkylamines, such as methylamine, dimethylamine, and triethylamine; mono-, di- or trihydroxyalkylamines such as mono-, di-, and triethanolamine; amino acids, such as arginine and lysine; guanidine; N-methylglucosamine; N-methylglucamine; L-glutamine; N-methylpiperazine; morpholine; ethylenediamine; N-benzylphenethylamine; (trihydroxymethyl)aminoethane; and the like. See, for example, J. Pharm. Sci., 66:1-19 (1977).

A "patient," "subject," or "host" to be treated by the subject method may mean either a human or non-human animal, such as primates, mammals, and vertebrates.

The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

The phrases "systemic administration," "administered systemically," "peripheral administration" and "administered peripherally" are art-recognized, and include the administration of a subject composition or other material other than directly into the central nervous system, e.g., by subcutaneous administration, such that it enters the patient's system and, thus, is subject to metabolism and other like processes.

The phrase "therapeutically effective amount" is an art-recognized term. In certain embodiments, the term refers to an amount of the therapeutic agent that, when used alone or in combination with a suitable matrix of the present invention, produces some desired effect at a reasonable benefit/risk ratio applicable to any medical treatment. In certain embodiments, the term refers to that amount necessary or sufficient to control the formation and/or stabilization of blood vessels. The effective amount may vary depending on such factors as the disease or condition being treated, the particular targeted constructs being administered, the size of the subject or the severity of the disease or condition. One of ordinary skill in the art may empirically determine the effective amount of a particular compound without necessitating undue experimentation. The exact formulation, route of administration and dosage for the composition and pharmaceutical compositions disclosed herein can be chosen by the individual physician in view of the patient's condition. (See, e.g., Fingl et al. 1975, in "The Pharmacological Basis of Therapeutics", Chapter 1, which is hereby incorporated herein by reference in its entirety). The dosage may be a single one or a series of two or more given in the course of one or more days, as is needed by the patient. Where no human dosage is established, a suitable human dosage can be inferred from $ED_{50}$ or $ID_{50}$ values, or other appropriate values derived from in vitro or in vivo studies, as qualified by toxicity studies and efficacy studies in animals. Dosage intervals can also be determined using MEC value. Compositions should be administered using a regimen which maintains plasma levels above the MEC for approximately 10% and approximately 90% of the time, preferably between approximately 30% and approximately 90%, and most preferably between approximately 50% and approximately 90%.

The amount of FGF-9 composition of the invention required for administration to provide a therapeutic effect varies as is understood by one of skill in the art and may vary depending on the embodiment of the invention; used in vitro, in vivo systemically, in vivo locally; in conjunction with a biomaterial; in an in vivo extended release format. Therefore, in some aspects the dosage may be from about 0.1 ng/ml to 100 ng/ml. In other aspects the dosage may be up to about 500 ng/ml. In still other aspects the amount may range up to about 1 mg/kg to about 100 mg/kg. It is understood by those of skill in the art that the amount of FGF-9 composition of the invention may be selected from any sub-range of the therapeutic dosages described herein: up to 0.01 ng/ml, up to 500 ng/ml. Dosages expressed by weight may also cover up to about 1 mg/kg to about 1000 mg/kg range, such as for example but not limited to; 1 mg/kg-500 mg/kg; 1 mg/kg-250 mg/kg; 1 mg/kg-200 mg/kg; 1 mg/kg-150 mg/kg; 1 mg/kg-75 mg/kg; 1 mg/kg-50 mg/kg; and 1 mg/kg-25 mg/kg and any sub-ranges of any of these ranges. Again, it is also possible that the amount may be greater than 1000 mg/kg and in some aspects less than 1 mg/kg.

In one embodiment, the pharmaceutical FGF-9 compositions provided herein may be formulated as controlled-release compositions, i.e. compositions in which the FGF-9 and other angiogenic polypeptide(s) is released over period of time after administration. Controlled- or sustained-release compositions include formulation in lipophilic depots (e.g. fatty acids, waxes, oils). In another embodiment, the composition is an immediate-release composition, i.e. a composition in which all of the FGF-9 and other angiogenic polypeptide(s) is released immediately after administration.

In yet another embodiment, the pharmaceutical compositions of the invention can be delivered in a controlled release system. For example, the FGF-9 composition comprising angiogenic polypeptide(s) may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321: 574 (1989). In another embodiment, polymeric materials can be used. In yet another embodiment, a controlled release system can be placed in proximity to the therapeutic target, i.e., the brain, thus requiring only a fraction of the systemic dose (see, e.g., Goodson, in Medical Applications of Controlled Release, supra, vol. 2, pp. 115-138 (1984). Other controlled-release systems are discussed in the review by Langer (Science 249:1527-1533 (1990). The compositions of the invention may also include incorporation of FGF-9 active into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts.) Such compositions will influence the physical state, solubility, stability, rate of in vivo release, and rate of in vivo clearance.

Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

Also embodied by the invention are the FGF-9 compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. The modified compounds are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

In a non-limiting embodiment, a localized medical device or biodegradable implant may be used to includes the functionality of time-course release of the compositions of the invention. The medical device may be composed of a solid casing with internal gel-like fluid containing the FGF-9 compositions of the invention. The gel-like fluid may be a cryoprecipitate, an administration matrix, or a composition of various polymers suitable for the sustained release of the composition. The biodegradable implant contains a biodegradable delivery means, or carrier, as well as the FGF-9 compositions of the invention. The carrier may be chosen so as to remain within the implanted site for a prolonged period and slowly release the angiogenic factors contained therein to the surrounding environment. This mode of delivery allows the FGF-9 compositions of the invention to remain in therapeutically effective amounts within the site for a prolonged period.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

Example 1

FGF-9 Variants

FGF-9 sequences and variants thereof may be derived from various naturally occurring sources. For example, FIG. 1 shows nucleic acid sequences encoding Human, Mouse and Rat FGF-9 retrieved from GenBank. As another example, FIG. 2 shows a multiple sequence alignment of Human, Mouse, Rat, and Pig FGF-9 amino acid sequences. Species specific amino acid sequences of FGF-9 retrieved from GenBank were aligned using JalView 2.3. A high degree of conservation in the amino acid sequence can be observed.

Variants of the FGF-9 sequences shown in FIG. 1 or 2 can be produced using known methods such as those described in Sambrook J et al. 2000. Molecular Cloning: A Laboratory Manual (Third Edition). Variants may be tested for the ability of wrapping and/or stabilizing a blood vessel.

Example 2

High Throughput Screening for Factors Secreted by SMCs as they Acquire Specialized Functions Human SMCs were subjected to serum deprivation for 8 days. This process converts SMCs to a state whereby they migrate in a specialized pattern. SMCs acquiring this specialized phenotype typically possess the ability of wrapping and stabilizing blood vessels. RNA harvested at days 0 and 8 was subsequently subjected to high density microarray analysis using Affymetrix U133 arrays. Three biological replicates were performed.

Analysis of microarray data revealed that of 1087 secreted factors expressed by SMCs only 27 were statistically upregulated as SMCs acquired the specialized phenotype. Of the 27 upregulated genes, FGF-9 was the most upregulated. The upregulation of FGF-9 was confirmed at the protein level as shown in FIG. 3.

Example 3

FGF-9 is Upregulated as SMCs Acquired Specialized Functions

Human SMCs were subjected to serum deprivation for 8 days. This process converts SMCs to a state whereby they migrate in a specialized pattern. SMCs acquiring this specialized phenotype typically possess the ability of wrapping and stabilizing blood vessels. RNA harvested at days 0 and 8 was subsequently subjected to high density microarray analysis.

As shown in FIG. 4 expression of FGF-3, 6, 8, 10, 13, 17, 19, 20, 22 and FGFR-4 was not detected. Expression of FGF-7, 11, 12, 14, 18 and FGFR-1, 2, and 3 was detected but did not change in response to serum withdrawal. FGF-1, 2 and 5 were downregulated in response to serum withdrawal while FGF-9 was upregulated as SMCs acquired the specialized phenotype.

Example 4

FGF-9 does not Initiate the Angiogenic Process in Subcutaneously Implanted Matrigel in Mice Matrigel plugs were mixed with either 500 ng/mL FGF-9, 500 ng/mL FGF-2 or 500 ng/mL FGF-2 and 200 ng/mL FGF-9 and subcutaneously injected into 3 month old C57/Bl6 mice. Mice were sacrificed and matrigel plugs were harvested 8 days after implantation and immunostained for CD31 (brown), to identify endothelial cell-lined microvessels.

FIG. 5 shows the results of this experiment. FGF-9 alone did not induce angiogenesis as indicated by an absence of CD31 immunoreactivity inside the matrigel (FIG. 5A).

FGF-2 (FIG. 5B) and FGF-2+FGF-9 (FIG. 5C) both induce angiogenesis in the matrigel as indicated by CD31 immunoreactivity (brown).

CD31-positive microvessels immunostained in FIGS. 5B and 5C are quantified. Graphical representation of the area of CD31-positive microvessels as shown in FIG. 5D indicates that equivalent levels of angiogenesis occur in matrigel plugs containing FGF-2 (FIG. 5B) and FGF-2+FGF-9 (FIG. 5C).

5E FGF-9 stimulates the formation of perfusable vessels. Mice bearing matrigel plugs containing FGF-2 or FGF-2+FGF-9 for 7 days were sacrificed and perfused with microfil and subjected to Three-dimensional (3D) micro-computed tomography (micro CT). The graph depicts the depth to which perfusable vessels penetrated the matrigel plug and demonstrates that vessels formed in matrigel containing FGF-2+FGF-9 were more functional and had a higher degree of perfusion compared to FGF-2 alone.

Example 5

FGF-9 Stimulates Recruitment of SM α-Actin Expressing Mural Cells to Nascent Microvessels During Angiogenesis Photomicrographs of 8 μm-thick sections of Matrigel plugs harvested 8 days after implantation into C57/Bl6 mice and immunostained for CD31 (brown) and smooth muscle α-actin (red) and quantification of the percentage of microvessels supported by smooth muscle (SM) α-actin positive cells.

Figure 6:
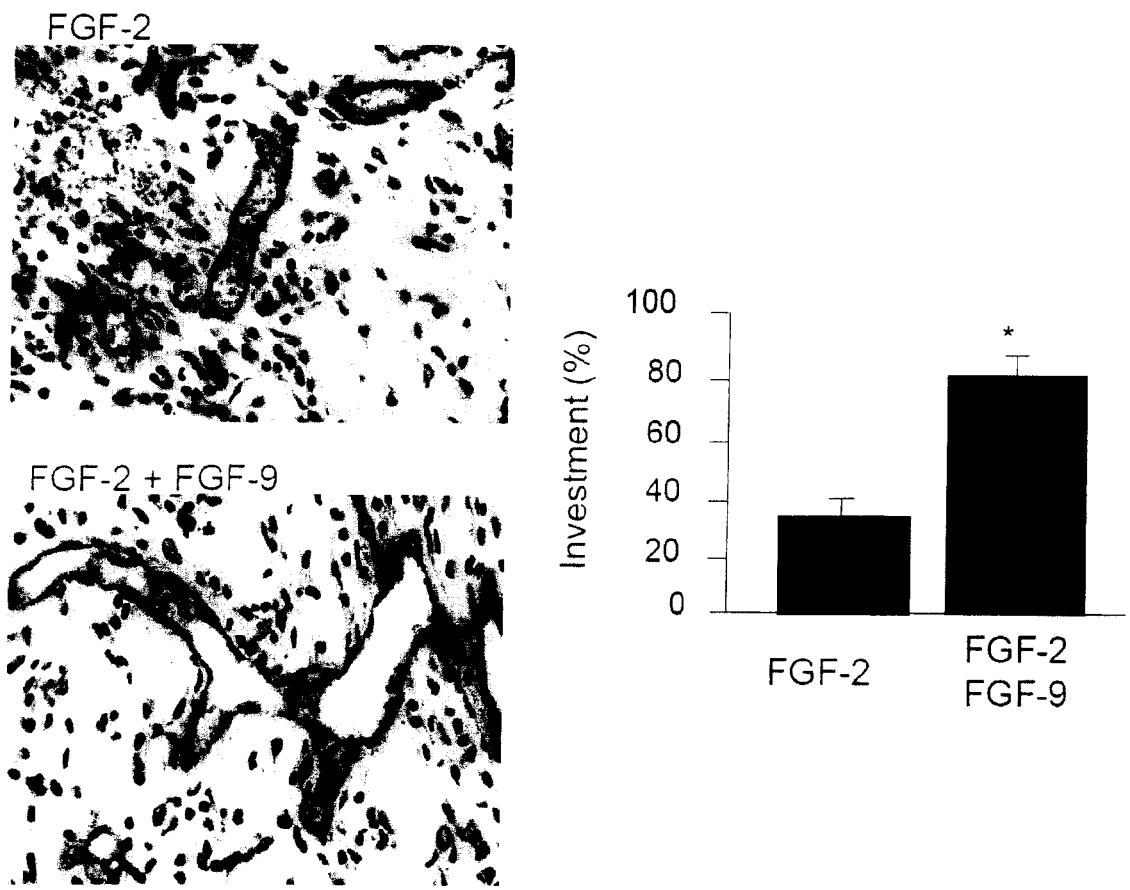
FIG. 6 shows that FGF-9 stimulates recruitment of SM α-actin expressing mural cells to nascent microvessels during angiogenesis.

FGF-9 induced the recruitment of smooth muscle α-actin positive cells around CD31-positive microvessels to a substantially greater extent than FGF-2 alone. Quantification of investment of nascent blood vessels by SM α-actin positive cells, as shown in the graph in FIG. 6, confirmed that FGF-9 stimulated the recruitment of smooth muscle around microvessels to a much greater extent than FGF-2 alone (83±7.7% vs. 37±5.4% P<0.05).

Example 6

FGF-9 Stimulates SM α-Actin Expressing Mural Cells Recruitment Along Continuous Lengths of Blood Vessels Photomicrographs of Matrigel plugs harvested 8 days after implantation, cut into 200 μm thick-sections and immunostained for CD31 (left panel) and SM α-actin (central panel) and quantitation of SM α-actin coverage of CD31-positive vessels.

Figure 7:
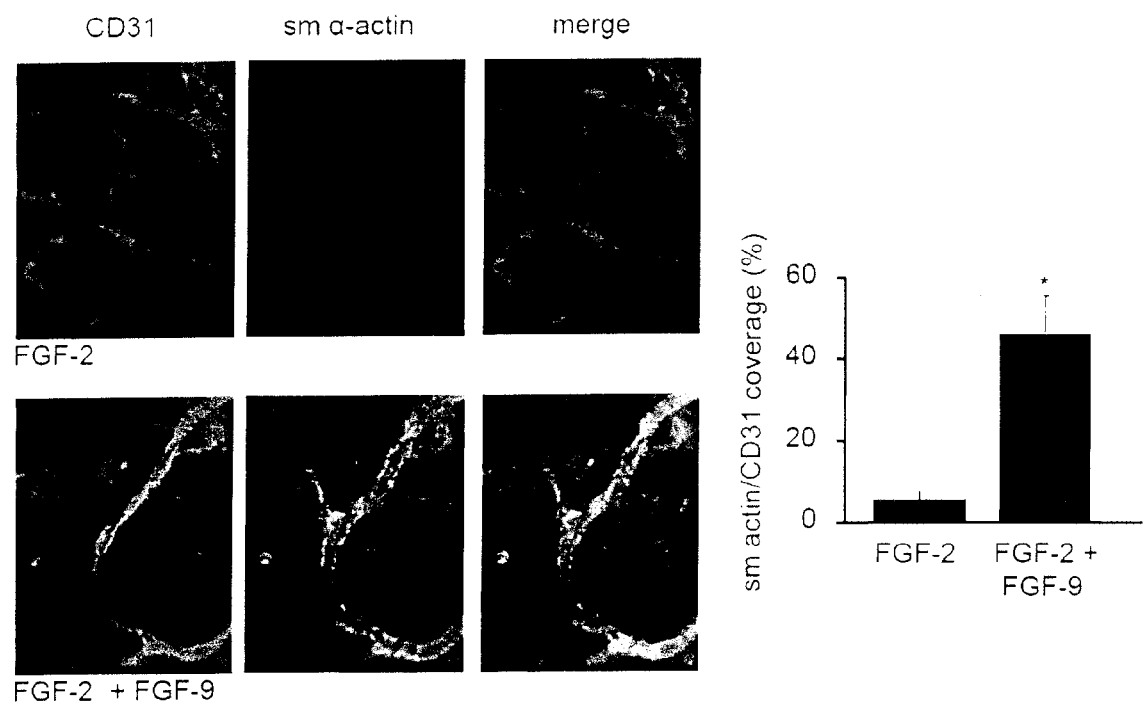
FIG. 7 shows that FGF-9 stimulates SM α-actin expressing mural cells recruitment along continuous lengths of blood vessels.

FGF-9 induced SM α-actin positive cells to associate along large length of nascent microvessels. Quantification of SM α-actin positive cell coverage of CD31 nascent blood vessels, as shown in the graph in FIG. 7, revealed that FGF-9 induced significantly more coverage compared to FGF-2 (45.4±5.3% vs. 7.2±1.8% P<0.05).

Example 7

FGF-9 Stimulates Circumferential Wrapping of Blood Vessels by SM α-Actin Expressing Mural Cells Confocal microscopy of FGF-2+FGF-9 matrigel plugs harvested 8 days after implantation. Sequential images, 1 μm thick, along the z-axis were collected to obtain 90 μm thick z-stack depicting the vessel.

Figure 8:
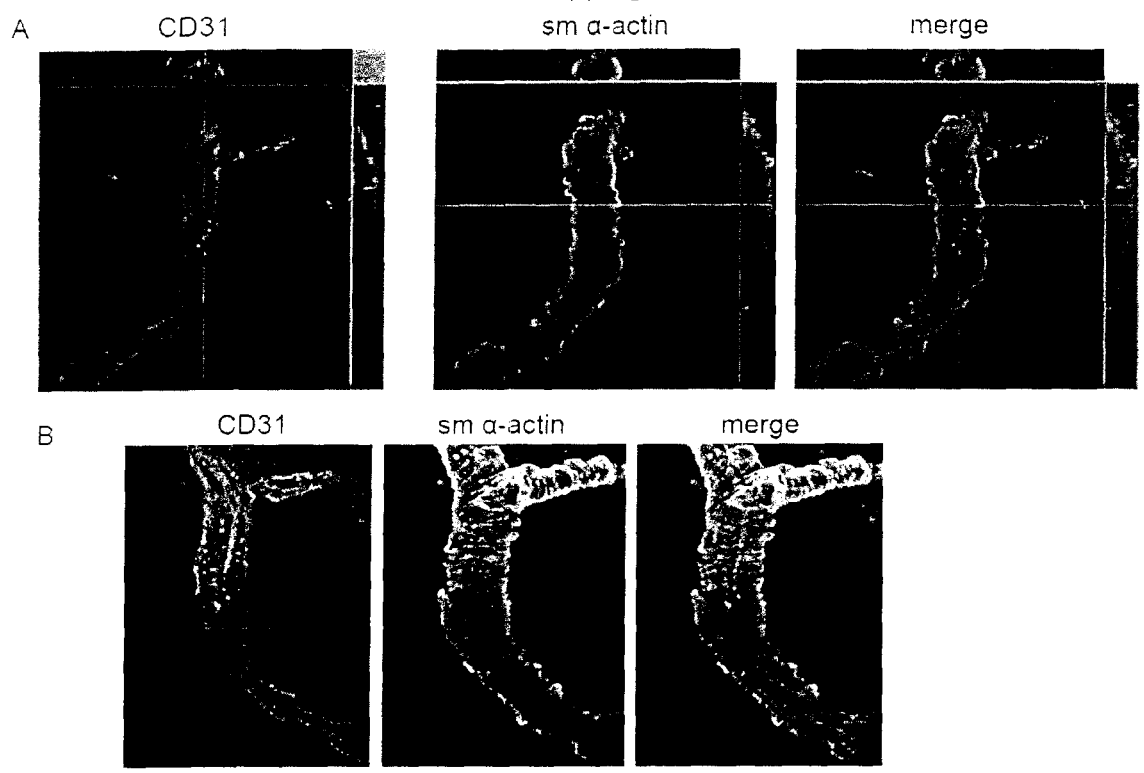
FIG. 8 shows that FGF-9 stimulates circumferential wrapping of blood vessels by SM α-actin expressing mural cells.

FIG. 8A shows orthogonal views of CD31-positive endothelial cells (left panel) and SM α-actin mural cells (central panel). FIG. 8B shows a three dimensional reconstruction of a 90 μm thick z-stack composed of 1 μm thick images.

The orthogonal views depict tight association between endothelial and supporting SM α-actin mural cells along the length of the vessel. The three dimensional reconstruction of the entire z-stack of this vessels illustrated that the actin positive mural cells circumferentially wrapped around the blood vessel, reminiscent of the organization found in vivo. This highlights the intimate and structurally cohesive association of SM α-actin expressing mural cells with blood vessels implying physiologic stabilization.

Example 8

FGF-9-Modified Microvessels are Responsive to Vasoactive Stimuli and can Vasodilate and Vasoconstrict 14 days after matrigel injection mice were anesthetized, the skin overlying a matrigel was surgically removed and a catheter to deliver drugs was sutured in the region of the plug. FITC-labeled dextran was injected via tail vein and the diameter of vessels in the matrigel plug was visualized using an inverted fluorescent microscope. Doses of vasoconstrictors indicated in FIG. 9 were applied and images of vessels were acquired over 5 minutes.

Figure 9:
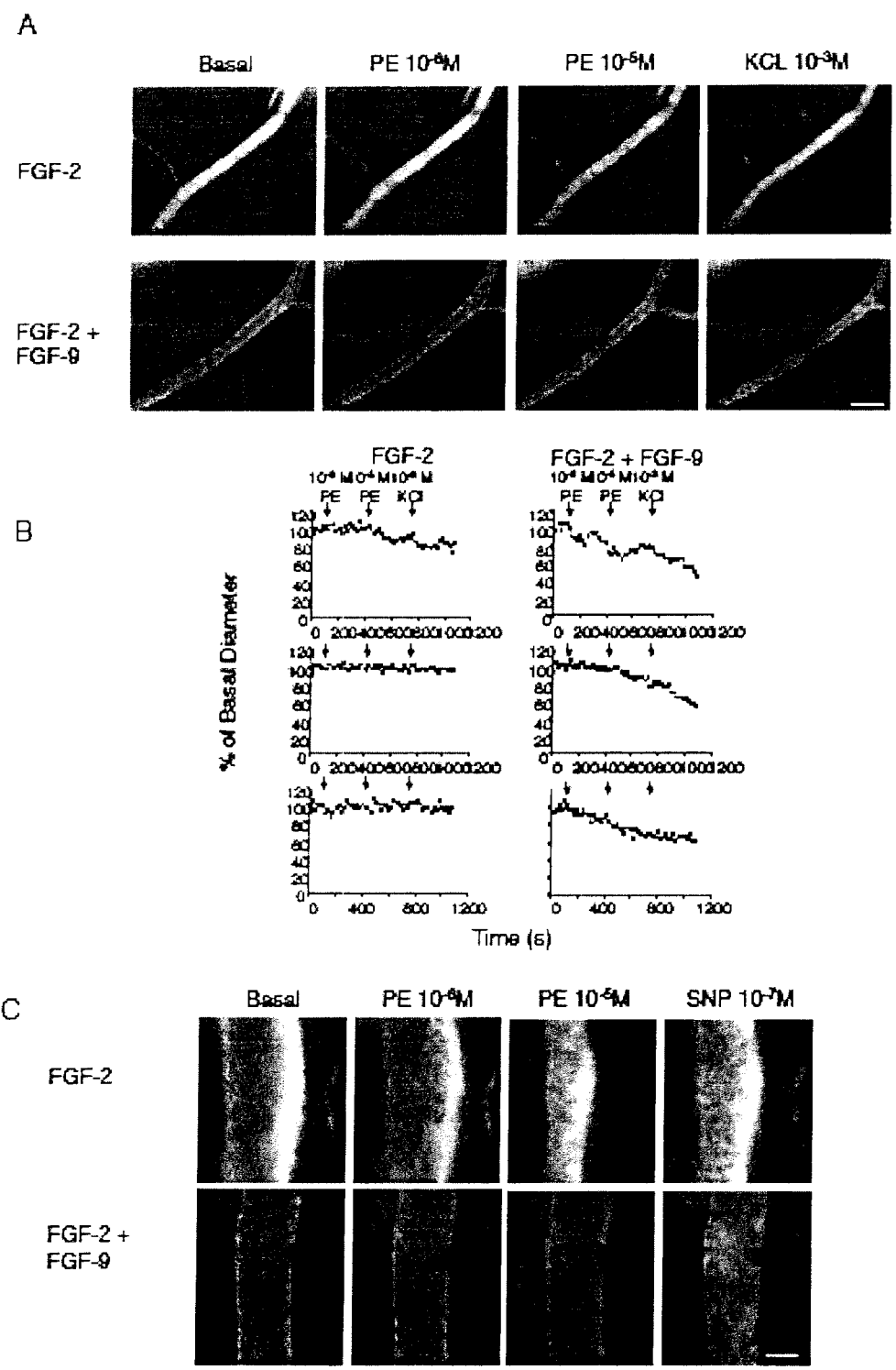
FIGS. 9A-C shows that FGF-9 modified microvessels are responsive to vasoactive stimuli and can vasoconstrict and vasodilate.

Representative tracings from separate mice, of the change in vessel diameter over time in response to phenylephrine (PE) and KCl are shown in FIG. 9. FGF-9-modified microvessels exhibited larger constrictions in response to PE and KCl compared to FGF-2 induced microvessels.

The tracings in FIG. 9B depict the change in vessel diameter in response to phenylepherine and KCl treatment. KCl will depolarize SMCs and result in receptor independent constriction if they are present on the blood vessels. FGF-2 induced vessels exhibit mild if any response to vasoconstrictors while the diameter of FGF-9 vessels is reduced by up to 65% of their initial diameter.

In separate experiments, doses of the vasoconstrictor PE followed by the vasodilator were applied to the blood vessels in matrigel plugs. Micrographs in C demonstrates that blood vessels in FGF-2+FGF-9 containing matrigel plugs constricted in response to PE and dilated in response to SNP.

Example 9

FGF-9-Stimulated Wrapping is Dependent on the Upregulation of PDGFR-β

Mouse dermal fibroblasts were stimulated with the doses of FGF-2 or FGF-9, indicated in FIG. 11A, for 24 h and then harvested. Cellular protein was separated by SDS-PAGE and the abundance of PDGFR-β was assessed by western blot analysis. As shown in FIG. 11A, FGF-9 induced the upregulation of PDGFR-β protein in mouse dermal fibroblasts.

Matrigel plugs containing either FGF-2 or FGF-2+FGF-9 were harvested 8 days after implantation and immunostained for PDGFR-β. As shown in FIG. 11B, PDGFR-β expression was markedly increased in matrigel plugs containing FGF-2+FGF-9 compared to FGF-2 alone.

Matrigel plugs containing either FGF-2 or FGF-2+FGF-9 in the presence of a PDGFR-β blocking antibody were harvested 8 days after implantation. The association of SM α-actin positive mural cells at blood vessels was assessed by immunostaining for CD31 and SM α-actin. The graph in FIG.

11C shows that blockade of PDGFR-β attenuates FGF-9-mediated recruitment of SM α-actin positive mural cells to nascent blood vessels compared to control antibody (18±4.4% vs. 87±4.3% p<0.05).

Example 10

FGF-9 Upregulates SMC Recruitment Proteins in vitro and in vivo

Figure 10:
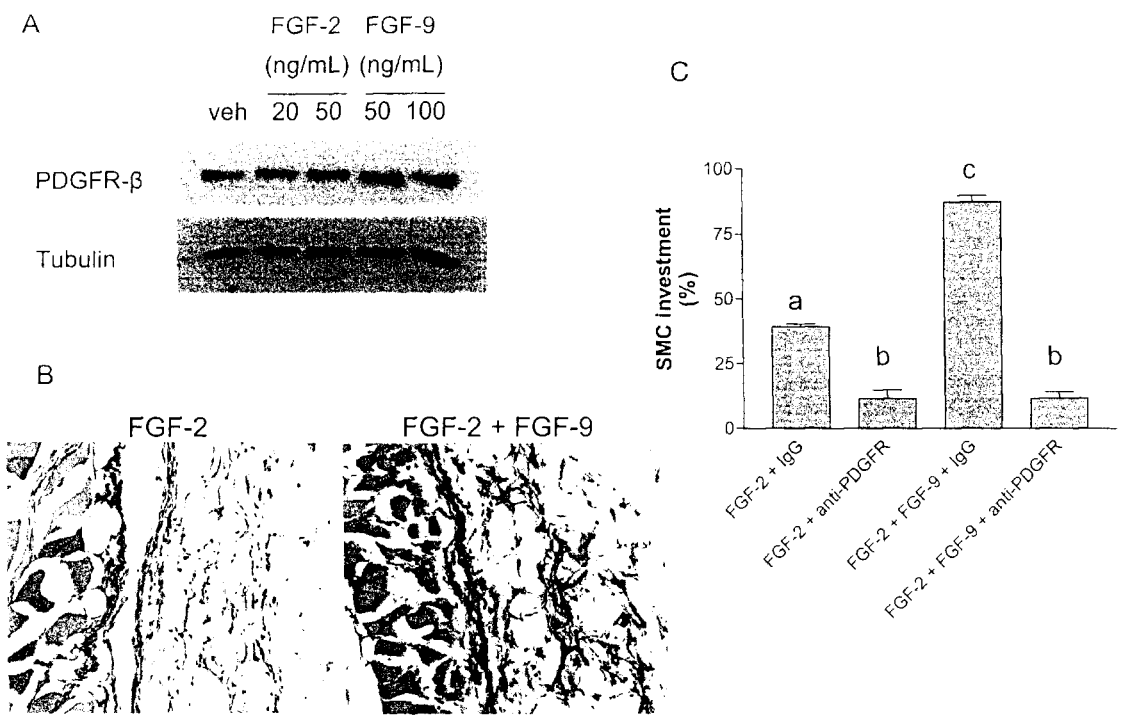
FIG. 10 shows that FGF-9-stimulated wrapping may be dependent on the upregulation of PDGFR-β.

A number of factors related to angiogenesis were screened in culture in an effort to identify mediators of FGF-9 effects. Several factors, including Vegf and TGF-beta1 were unaffected by FGF-9 treatment or overexpression. In contrast PDGFR-β, a mediator of SMC homing to endothelial cells was upregulated by FGF-9 treatment and overexpression in human smooth muscle cells and mouse dermal fibroblasts (FIG. 10A-C).

Also components of Sonic Hedgehog signaling, which are required for formation of arteries in zebrafish were also upregulated at the mRNA level. The upregulation of PDGFR-β by FGF-9 during angiogenesis was confirmed in vivo by immunohistochemistry (FIG. 10B). The effect of a PDGFR-β blocking antibody on SMC recruitment to nascent vessels in vivo was also tested.

Example 11

2- and 3-Dimensional Vasculogenesis Assay

Figure 11:
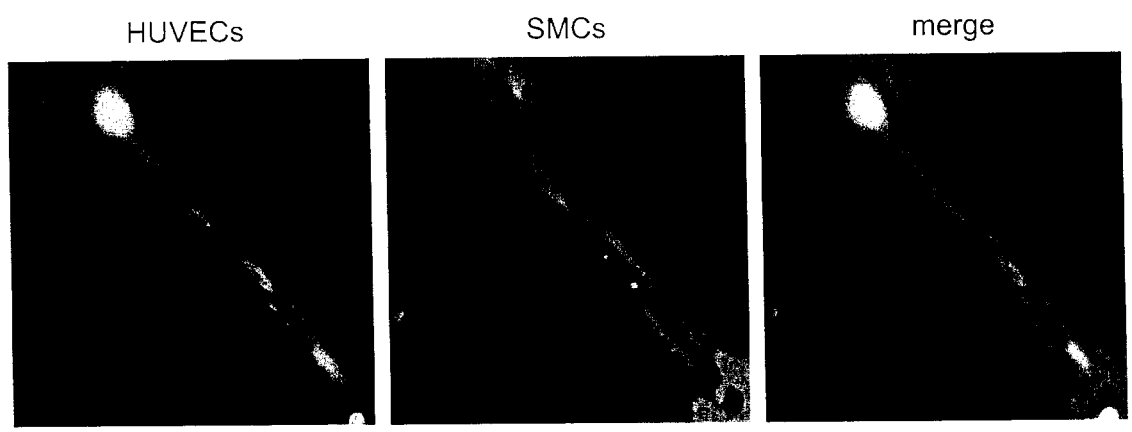
FIG. 11 shows vasculogenesis in an in vitro matrigel assay with endothelial and smooth muscle cells.

Human SMCs were treated with increasing doses of FGF-9 for 24 hr. Human umbilical endothelial cells expressing eGFP (green fluorescent protein) were plated onto growth factor-reduced matrigel coated dishes at a density of $1.5 \times 10^4$ cells/cm$^2$. After 4 hr human smooth muscle cells expressing mRFP (red fluorescent protein) were added at a density of $1.5 \times 10^4$ cells/cm$^2$ and the migration of SMCs to endothelial tubules was tracked microscopically for 24 h optionally in the presence of 100 ng/mL of FGF-9. Fluorescence photomicrographs depict the association of mRFP expressing SMCs with eGFP expressing endothelial tubules 10 h after addition of SMCs (FIG. 11).

Subsequently, endothelial cells and human SMCs will be co-cultured on matrigel, or within a matrigel or equivalent matrix using methodologies well known to someone skilled in the art (for example as described in Scaffolding in Tissue Engineering (eds. Ma, P. X. and Eliseeff, J), 2006 CRC Press, Boca Raton, Fla.), to produce two dimensional and 3-dimensional cultures respectively. The formation, activity, and stabilization of blood vessels in the cultures will be assayed. Supplemented in such cultures will be variations of and combinations of optimized concentrations of FGF2 and FGF9. Over time, the assembly of blood vessels and the extent of vasculogenesis will be tracked by time lapse microscopy, and properties evaluated by confocal microscopy. The reactivity of such vessels will be evaluated by methods already described herein.

Example 12

FGF-9 Stabilizes the Neovasculature and the Vessel Stabilization is Persistent Over Time A Photomicrographs of matrigel plugs (FIG. 12) harvested 1 year after implantation and immunostained for CD31 (brown). 12B Quantification of angiogenesis assessed as the area containing CD31 positive microvessels. FGF-2+FGF-9-containing matrigel plugs had significantly more vessels 1 year after implantation especially vessels with a diameter greater than 15 µM.

Example 13

FGF-9 Stimulates the Recruitment of Nerves to the Neovasculature

Figure 13:
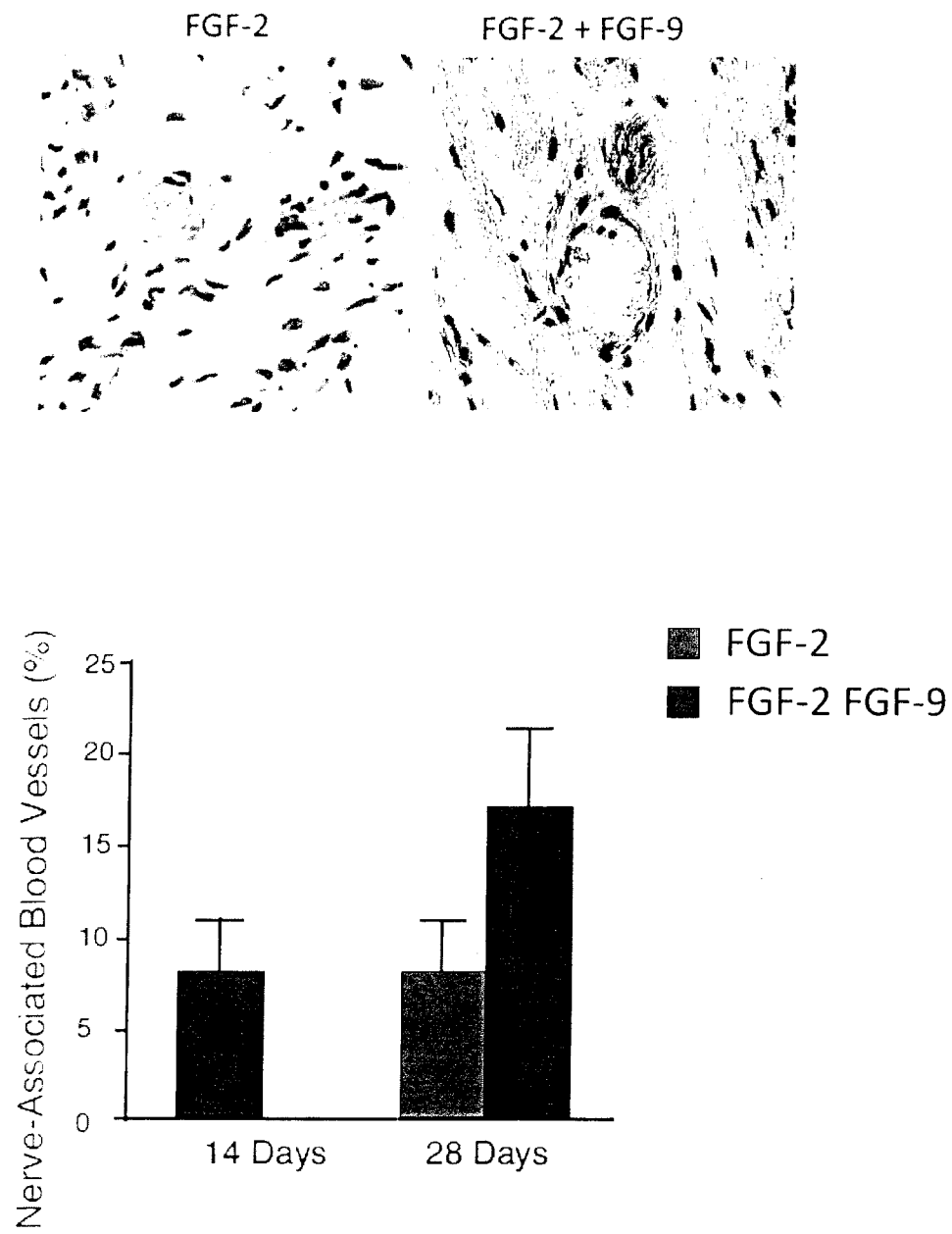
FIG. 13 shows that FGF-9 stimulates the recruitment of nerves to the neovasculature.

A. Photomicrographs (FIG. 13) of of matrigel plugs containing either FGF-2 or FGF-2+FGF-9 harvested 28 days after implantation and immunostained for the neurolfilament protein marker NF-200 to detect the presence of blood vessel-associated nerves. B. The graph depicts the percentage of nerved-associated blood vessels at 14 and 28 days after implantation.

Example 14

FGF-9-Stimulated Wrapping is Dependent on the Upregulation of PDGFR-β

Figure 14:
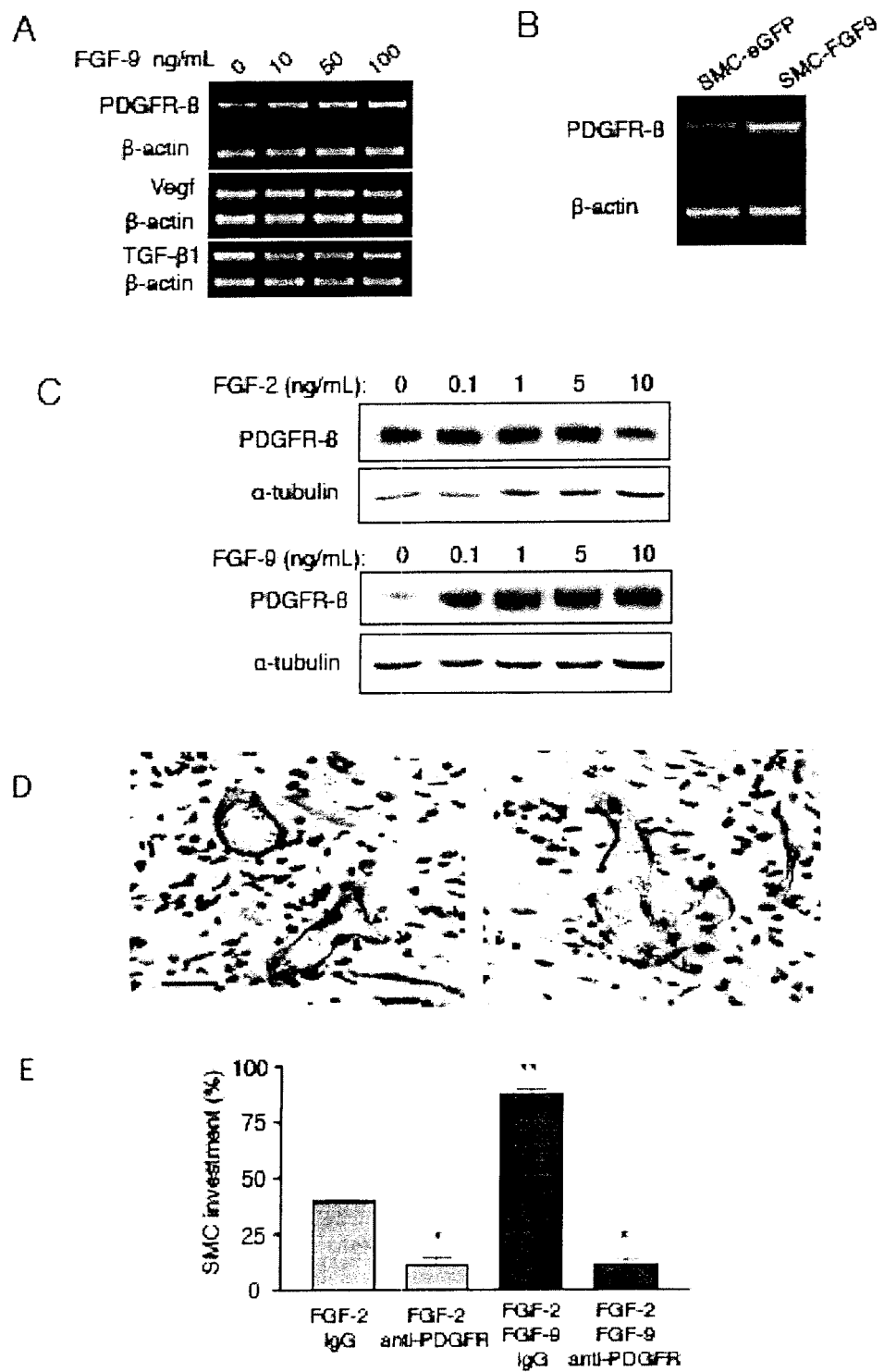
FIG. 14 shows that FGF-9-stimulated wrapping is dependent on the upregulation of PDGFR-β.

A. RT-PCR of human aortic SMCs (FIG. 14) stimulated with increasing concentrations of recombinant FGF-9 for 24 h. A number of genes involved in angiogenesis were assessed. With only PDGFR-β being upregulated B, RT-PCR of human aortic SMCs overexpressing cDNA encoding GFP or FGF-9. C, Western Blots of C57/Bl6 dermal fibroblasts treated with either FGF-2 or FGF-9 for 24 h.

Mouse dermal fibroblasts were stimulated with the doses of FGF-2 or FGF-9, indicated in FIG. 14C, for 24 h and then harvested. Cellular protein was separated by SDS-PAGE and the abundance of PDGFR-β was assessed by western blot analysis. As shown in FIG. 14B, in contrast to FGF-2, FGF-9 induced the upregulation of PDGFR-β protein in mouse dermal fibroblasts.

Photomicrographs of Matrigel plugs containing FGF-2+FGF-9 with either control IgG or PDGFR-β blocking antibody double immunolabeled for CD31 (brown) and sm α-actin (red) harvested 8 days after implantation. The presence of PDGFR-β blocking antibody attenuated the FGF-9 induced recruitment of sm α-actin positive cells to new blood vessels. E Quantitation of SM α-actin coverage of CD31-positive vessels in mice bearing FGF-2 or FGF-2+FGF-9 with either control IgG or PDGFR-β blocking antibody. The graph in FIG. 14E shows that blockade of PDGFR-β attenuates FGF-9-mediated recruitment of SM α-actin positive mural cells to nascent blood vessels compared to control antibody (18±4.4% vs. 87±4.3% p<0.05).

Example 15

Figure 15:
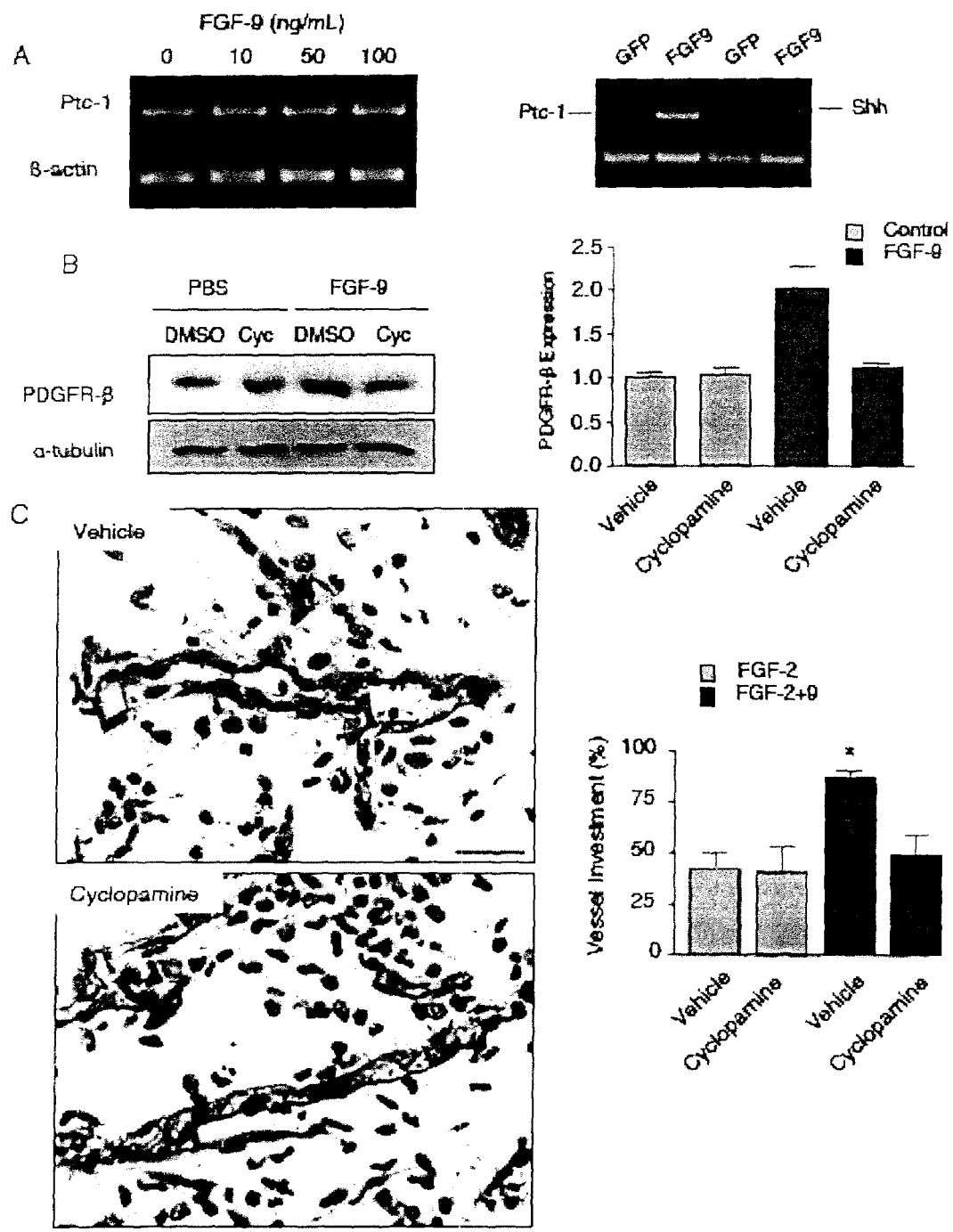
FIG. 15 shows that FGF-9-mediated PDGFR-β upregulation and vessel maturation requires Sonic Hedgehog signaling.

FGF-9-Mediated PDGFR-β Upregulation and Vessel Maturation Requires Sonic Hedgehog Signaling FIG. 15A. RT-PCR of human aortic SMCs stimulated with increasing concentrations of recombinant FGF-9 for 24 h. 15B, RT-PCR of human aortic SMCs overexpressing cDNA encoding GFP or FGF-9. 15C, Western Blots of C57/Bl6 dermal fibroblasts pretreated with either DMSO or 500 nM cyclopamine and subsequently stimulated with vehicle or FGF-9 for 24 hr. 15D. Photomicrographs of FGF-2 and FGF-9 containing matrigel plugs with either DMSO or cyclopamine double immunolabeled for CD31 (brown) and sm α-actin (red). E Quantitation of SM α-actin coverage of CD31-positive vessels representative of 6 mice bearing FGF-2 or FGF-2+FGF-9 with either vehicle or 500 nM cyclopamine (79±4 vs 38±4.8, p<0.05).

Example 16

In vitro Direct Effects on SMCS in Culture

Figure 16:
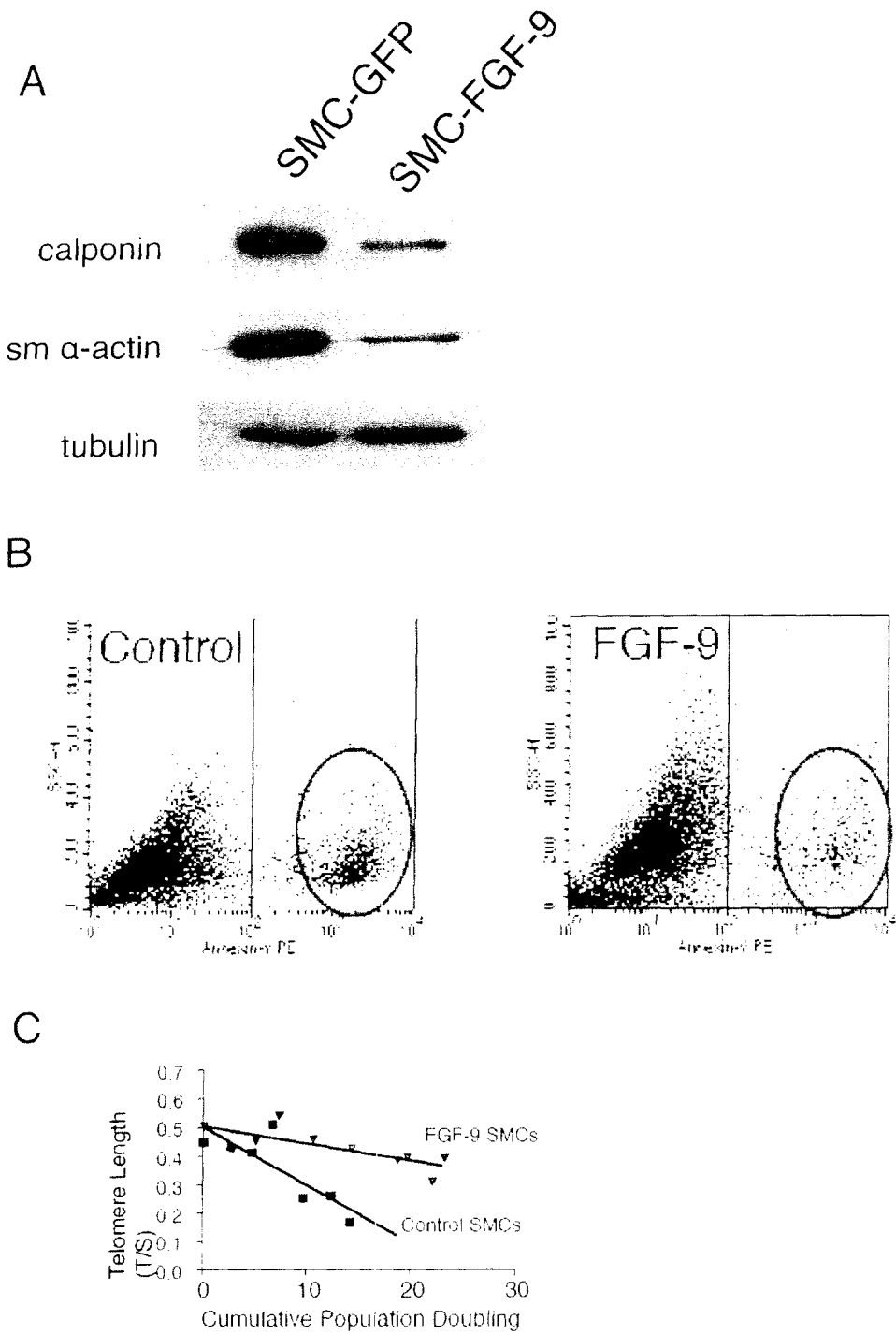
FIG. 16 shows the in vitro direct effects of FGF-9 on SMCs in culture.

FIG. 16A. Lysates of SMCs expressing either GFP or FGF-9 were subjected to Western blot analysis to assess levels of smooth muscle cell markers. SMCs expressing FGF-9 exhibited a more primitive and plastic phenotype compared to GFP expressing cultures as indicates by decreased levels of smooth muscle α-actin and calponin. 16B. SMCs expressing either GFP or FGF-9 were stained with Annexin to detect apoptotic cells and subjected to flow cytometry. Cultures of SMC expressing FGF-9 were less apoptotic as indicated by the smaller proportion of Annexin positive cells. C. SMCs expressing either GFP or FGF-9 were serially cultured and counted to determine their cumulative population doubling and DNA from each passage was isolated and subjected to real time PCR analysis to assess the rate of telomere attrition. The graph shows that cultures of SMCs expressing FGF-9 experienced a decreased rate of telomere decay compared to control SMCs.

Example 17

Schematic of Proposed Mechanism of Action for FGF-9 During Angiogenesis

Figure 17:
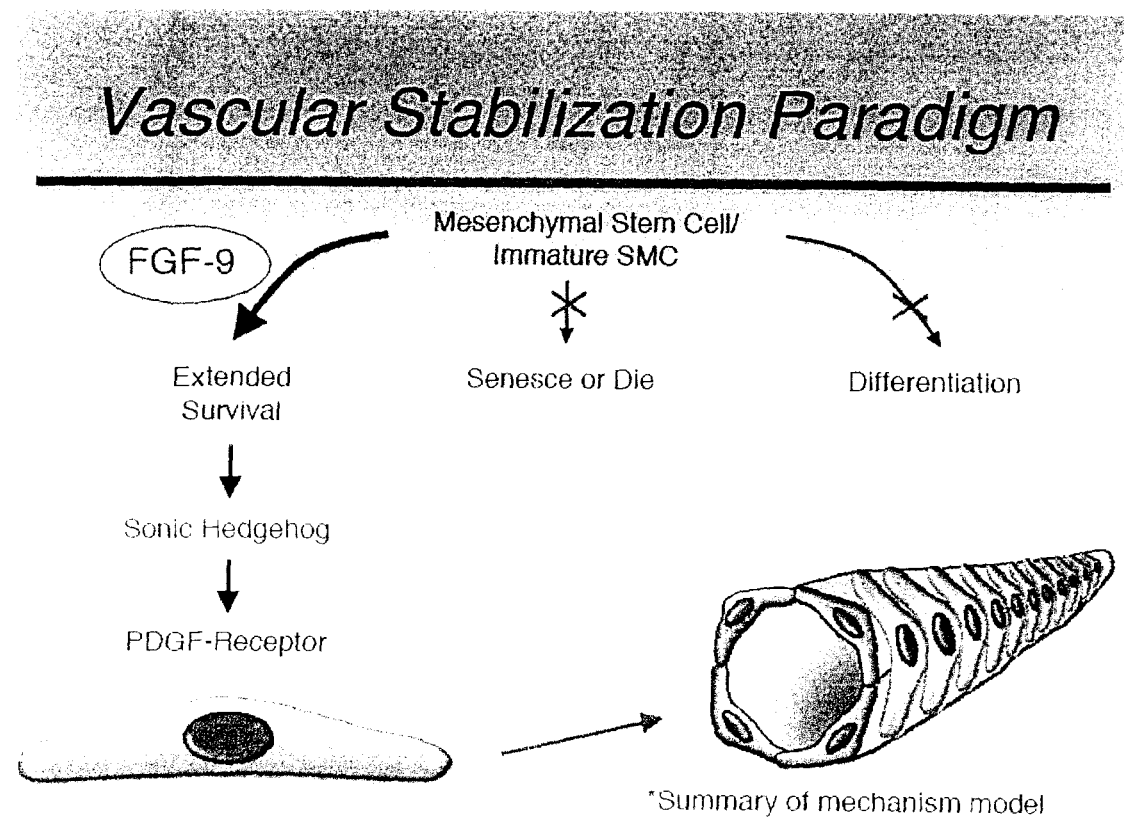
FIG. 17 shows the proposed mechanism of action for FGF-9 during angiogenesis.

FGF-9 signals to a pool of mesenchymal precursors and/or immature stem cells to enhance their survival, and prevent senescence. Through either a the same or an unrelated pathway, FGF-9 activates Sonic Hedgehog signaling to induce the upregulation of the PDGFR-β receptor on these mesenchymal cells. This increases the competence of this pool of cells to migrate to the ligand for this receptor, PDGF-bb which is secreted by endothelial cells forming new blood vessels. The recruitment of mesenchymal cells to blood vessels results in their maturation to SMC cells which are capable of stabilizing the nascent microvasculature and imparting vasoresponsiveness (FIG. 17).

Example 18

Orthotopic Renal Cancer Model of Metastases

An animal model of metastatic cancer was generated. FGF-9 alone, or optionally in combination with another angiogenic molecule, was administered to mice to demonstrate utility in treatment of cancer. It is established that angiogenesis drives the growth of tumors and that the blood vessels formed in tumors lack supporting mural cells and are prone to leakage. A negative correlation has been established between vessels coverage and metastasis and poor survival in human colorectal cancers. Recent studies have functionally demonstrated that wrapping of tumor blood vessels can limit tumor cell metastasis.

Figure 18:
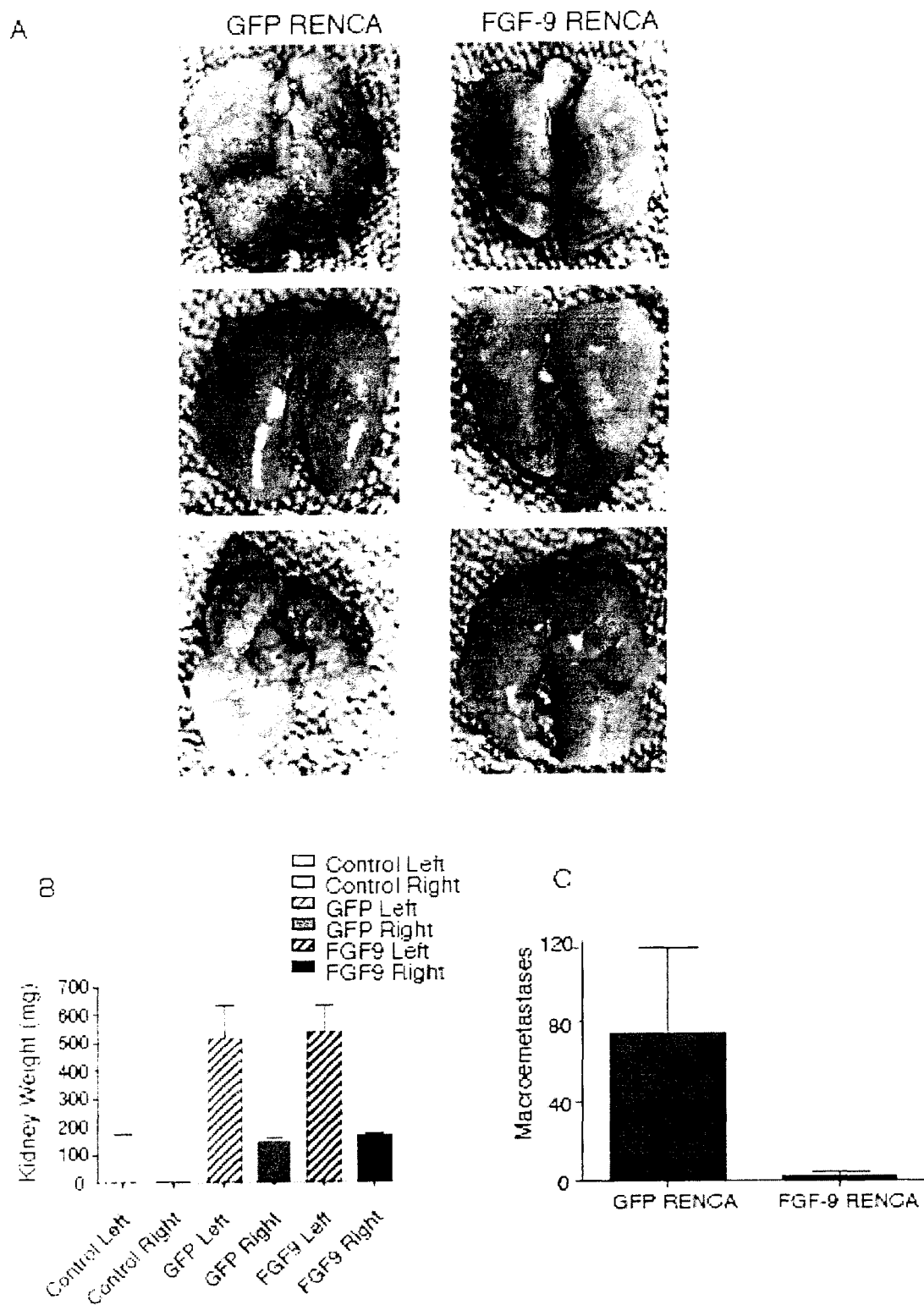
FIG. 18 shows a cancer model using a kidney carcinoma cell line to demonstrate the "tightening" of the blood vessel to prevent metastasis from primary tumors to distal sites.

Female Balb/c mice were injected in the subcapsular space of the left kidney with $5\times10^5$ RENCA cells expressing either GFP or FGF-9 suspended in growth factor reduced matrigel. After 14 days, both kidneys were excised and lungs were excised and assessed. FIG. 18A. Photographs of excised lungs from Balb/c mice bearing kidney tumors derived from either GFP- or FGF-9 expressing RENCA cells. Surface metastases can be identified as irregular translucent bulges/distentions/protruberance on the lung surface (arrows) and were more prevalent in GFP-RENCA bearing mice. 18B. Quantitation of kidney weight which indicates that there was no difference in the size of primary tumors in the left kidney of GFP expressing RENCA cells compared to FGF-9 expressing RENCA cells (514.9 mg±114.6 vs. 536.2 mg±95.4 n=6 GFP vs. FGF-9). 18C. The graph depicts the average number of surface metastases on the lungs of Balb/c mice with a trend towards a reduction in metastasis in mice bearing tumors derived from FGF-9 expressing RENCA cells (74±43 vs 2±4.3 n=6)

Example 19

In vitro Co-Culture

Figure 19:
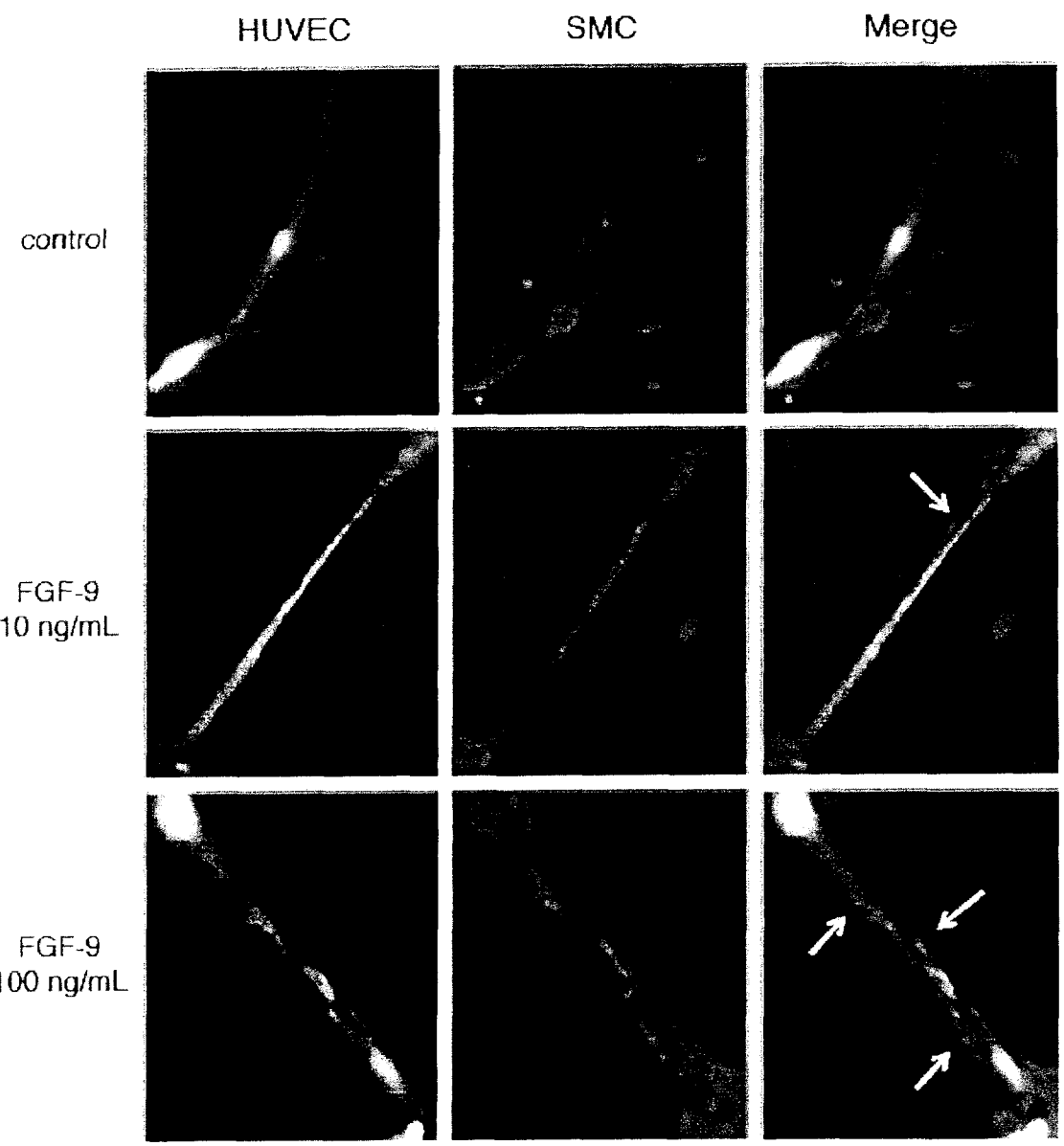
FIG. 19 shows in vitro co-culture and tubule formation using FGF-9.

HUVECs expressing EGFP were plated on growth factor reduced matrigel and allowed to adhere for 4 hr before the addition of HITC6 SMCs expressing mRFP, pretreated with the indicated doses of FGF-9 for 16 h, and fluorescent images were subsequently acquired 10 h later, arrows indicate RFP-positive SMCs aligned along GFP-positive endothelial tubules (FIG. 19). In control conditions few RFP-positive cells were associated with GFP-positive endothelial tubules while increasing concentrations of FGF-9 resulted in increasing association of SMCs with endothelial tubules.

Example 20

In vitro Endothelial Tubules

Figure 20:
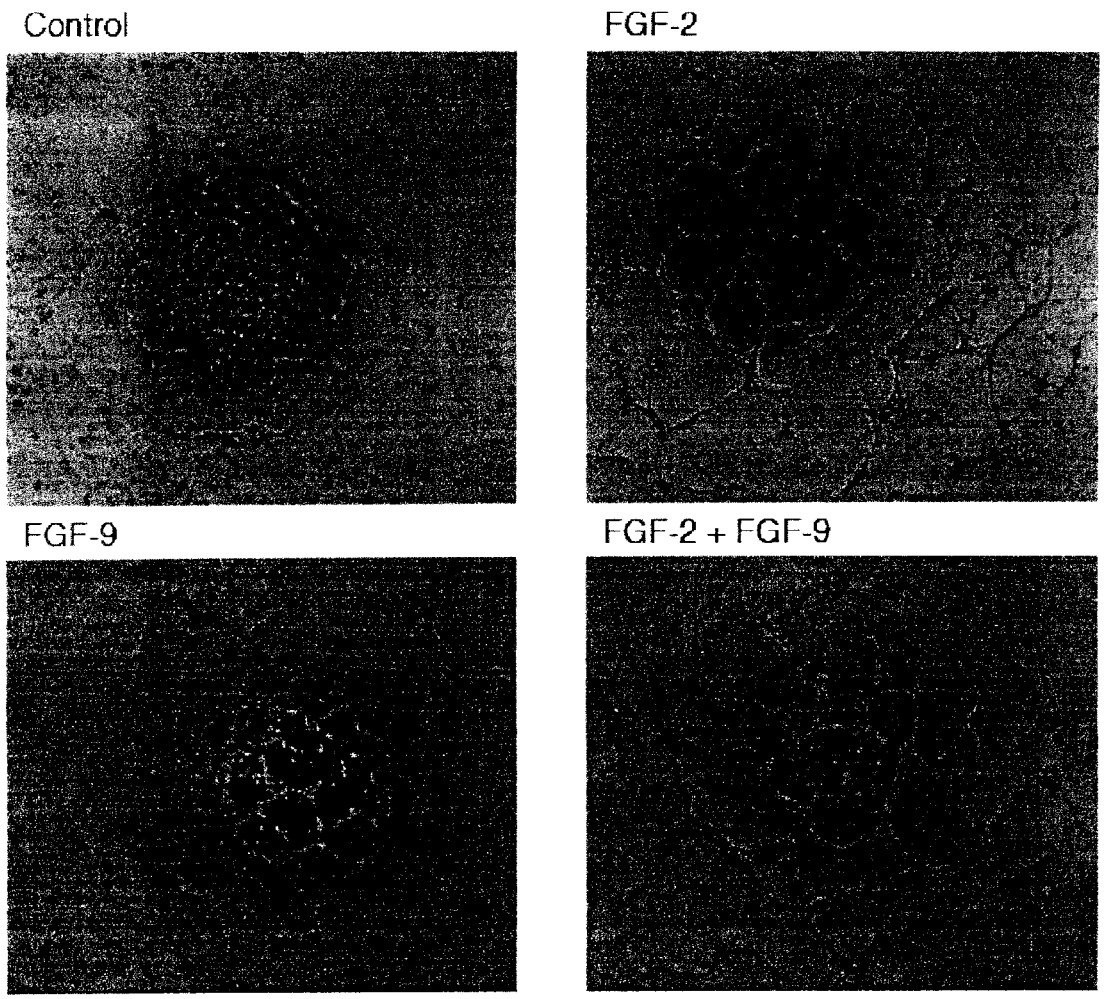
FIG. 20 shows that FGF-9 results in increased association of SMCs with endothelial tubes.

HUVECs expressing EGFP were plated on growth factor reduced matrigel and allowed to adhere for 4 hr before the addition of HITC6 SMCs expressing mRFP, pretreated with the indicated doses of FGF-9 for 16 h, and fluorescent images were subsequently acquired 10 h later, arrows indicate RFP-positive SMCs aligned along GFP-positive endothelial tubules (FIG. 20). In control conditions few RFP-positive cells were associated with GFP-positive endothelial tubules while increasing concentrations of FGF-9 resulted in increasing association of SMCs with endothelial tubules. This together with the results shown in FIGS. 16B and 16C demonstrates better cell survival resulting in vessel formation.

The above-described embodiments are intended to be examples and alterations and modifications may be effected thereto, by those of skill in the art, without departing from the scope of the invention which is defined by the claims appended hereto.

What is claimed is:

1. A method of promoting formation of mature blood vessels in a subject or treating ischemia, the method comprising administering an effective amount of a composition comprising FGF-9 polypeptide and FGF-2, wherein said FGF-9 polypeptide has an amino acid sequence selected from the group consisting of: SEQ ID NO:1, SEQ ID NO:2, SEQ ID NO:3 and SEQ ID NO:4, or a variant thereof, wherein said variant is at least 96% or 98% identical to the amino acid sequence selected from the group consisting of SEQ ID NO:1, SEQ ID NO:2, SEQ ID NO:3 and SEQ ID NO:4 to the subject.

2. The method of claim 1, wherein said blood vessels are within a tumor.

3. A method of promoting formation or stabilization of blood vessels in a subject comprising administering an effective amount of a composition of comprising FGF-9 polypeptide and FGF-2, said FGF-9 having an amino acid sequence selected from the group consisting of: SEQ ID NO:1, SEQ ID NO:2, SEQ ID NO:3 and SEQ ID NO:4, or a variant thereof, wherein said variant is at least 96% or 98% identical to the amino acid sequence selected from the group consisting of SEQ ID NO:1, SEQ ID NO:2, SEQ ID NO:3 and SEQ ID NO:4 to the subject.

4. The method of claim 3, wherein said composition promotes proliferation and migration of endothelial cells to form immature vascular networks and the recruitment of mesenchymal cells including pericyte and/or smooth muscle cells to wrap the vessels to stabilize them.

5. The method of claim 4, wherein said stabilization improves the condition of said blood vessels.

* * * * *